United States Patent [19]

Matzuk

[11] 4,092,867
[45] June 6, 1978

[54] ULTRASONIC SCANNING APPARATUS

[76] Inventor: Terrance Matzuk, 154 Eileen Dr., Pittsburgh, Pa. 15214

[21] Appl. No.: 767,376

[22] Filed: Feb. 10, 1977

[51] Int. Cl.² ............................................. G01N 29/04
[52] U.S. Cl. ...................................... 73/609; 73/614; 73/619; 73/621; 73/633; 73/642; 128/2 V
[58] Field of Search ............ 73/67.8 S, 67.9, 71.5 US, 73/609, 614, 619, 621, 633, 642; 128/2 V, 24 A, 2.05 Z; 340/5 MP; 358/112

[56] References Cited

U.S. PATENT DOCUMENTS

| | | | |
|---|---|---|---|
| 870,938 | 11/1907 | Cove | 310/36 |
| 3,406,564 | 10/1968 | Phillips | 73/620 |
| 3,678,736 | 7/1972 | May | 73/67.8 S |
| 3,690,311 | 9/1972 | Schorum | 128/2 |
| 3,721,227 | 3/1973 | Larson et al. | 128/2 V |
| 3,765,229 | 10/1973 | Spencer et al. | 73/67.8 S |
| 3,784,805 | 1/1974 | Rolle | 340/3 |
| 3,789,833 | 2/1974 | Bom | 128/2 V |
| 3,927,661 | 12/1975 | Takemura | 128/2 V |
| 3,955,561 | 5/1976 | Eggleton | 128/2.05 Z |
| 3,974,826 | 8/1976 | Eggleton et al. | 128/2 V |
| 3,990,300 | 11/1976 | Kossoff | 73/67.8 S |

FOREIGN PATENT DOCUMENTS

461,349   4/1975   U.S.S.R. ......................... 73/71.5 US

Primary Examiner—Richard C. Queisser
Assistant Examiner—John P. Beauchamp
Attorney, Agent, or Firm—Arnold B. Silverman

[57] ABSTRACT

An ultrasonic scanner having a housing, an ultrasonic transducer disposed within the housing and mounted for movement in a predetermined path therewithin. Magnetic means are provided for effecting movement of the transducer in a predetermined path, and electrical means are provided for energizing the transducer and receiving signals therefrom.

The scanner may be servo-controlled and be provided with position sensing means for determining the position of the transducer within the predetermined path, and signal processing means for receiving feedback signals from said position sensing means and adjusting said transducer position responsive to said feedback signals indicating the existence of a departure from the desired transducer position.

46 Claims, 67 Drawing Figures

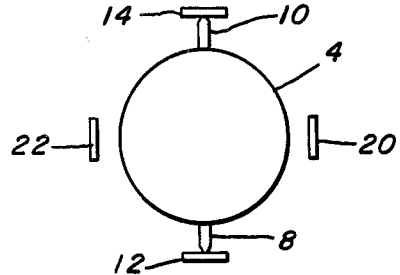
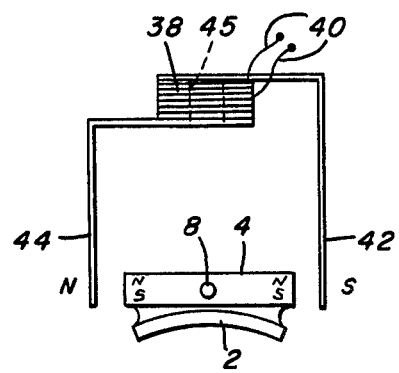
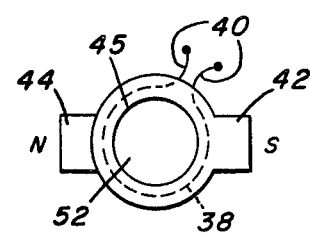
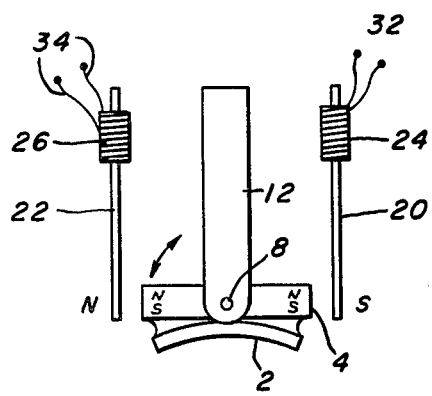
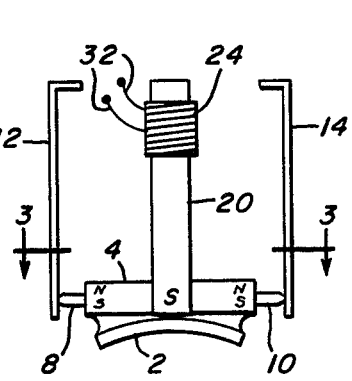
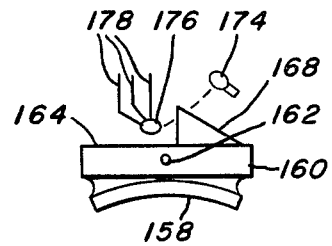
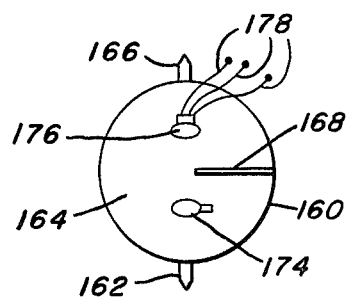
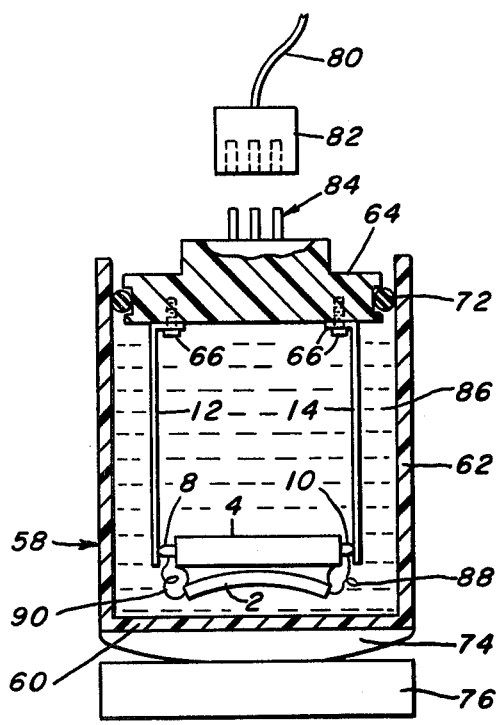
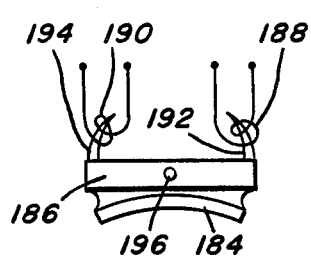
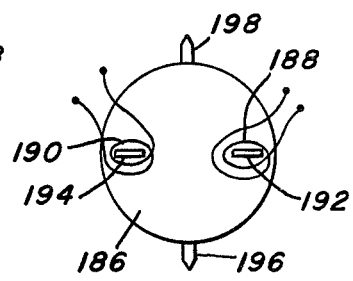

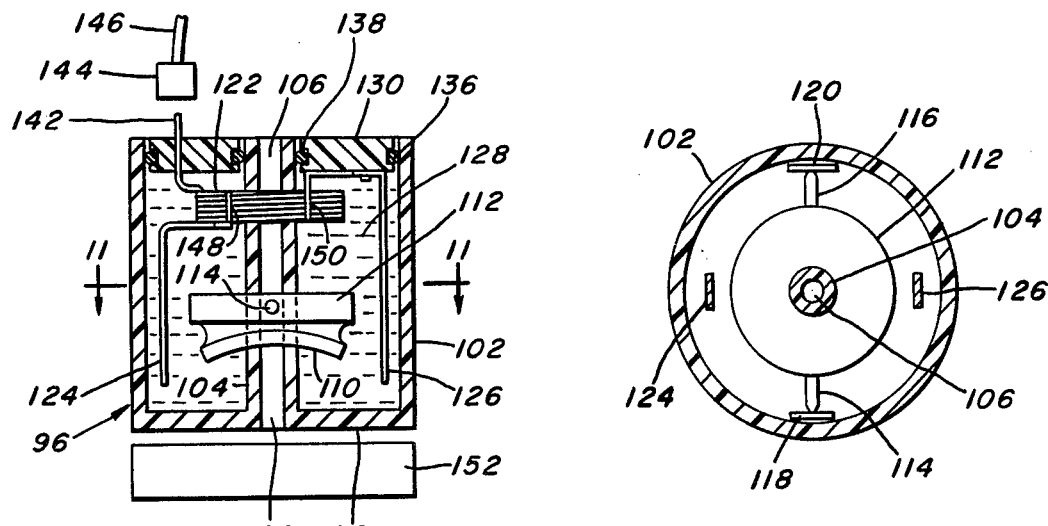
FIG. 10.
FIG. 11.
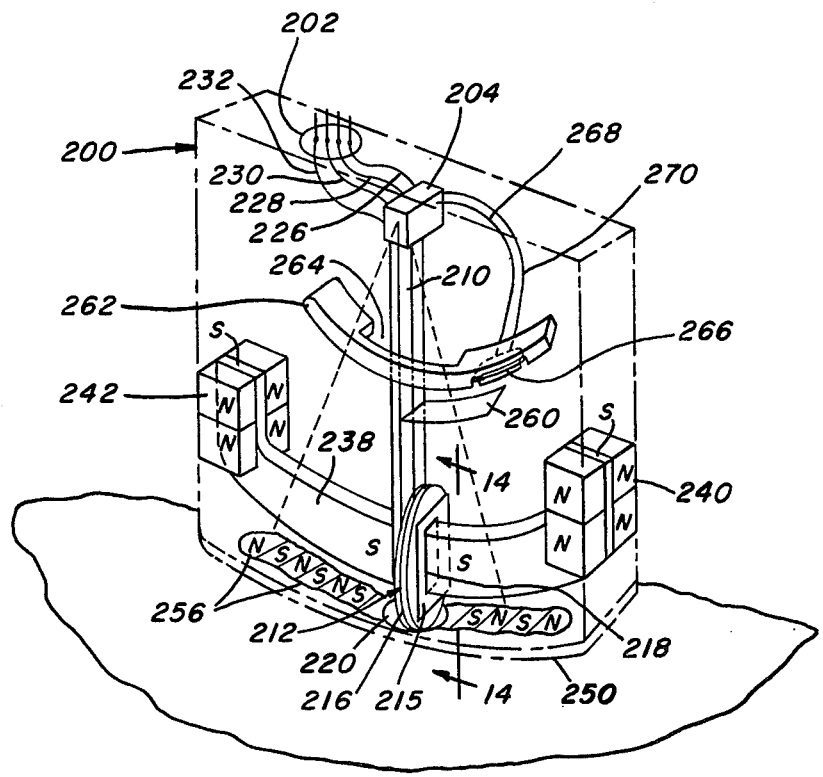
FIG. 12.

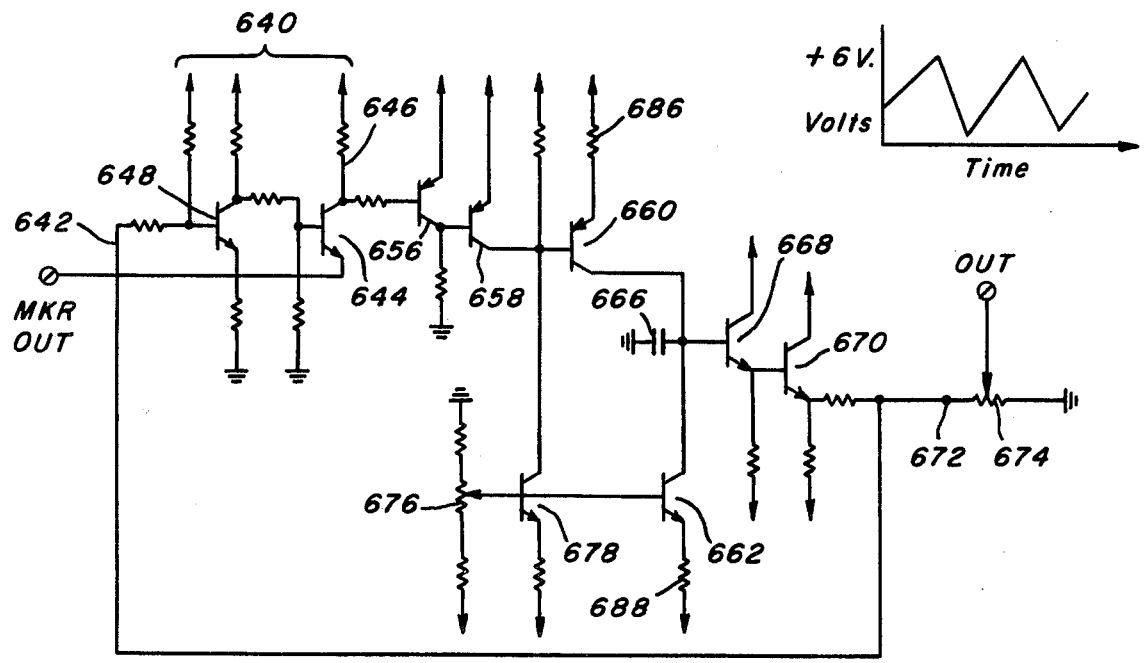
FIG. 26.
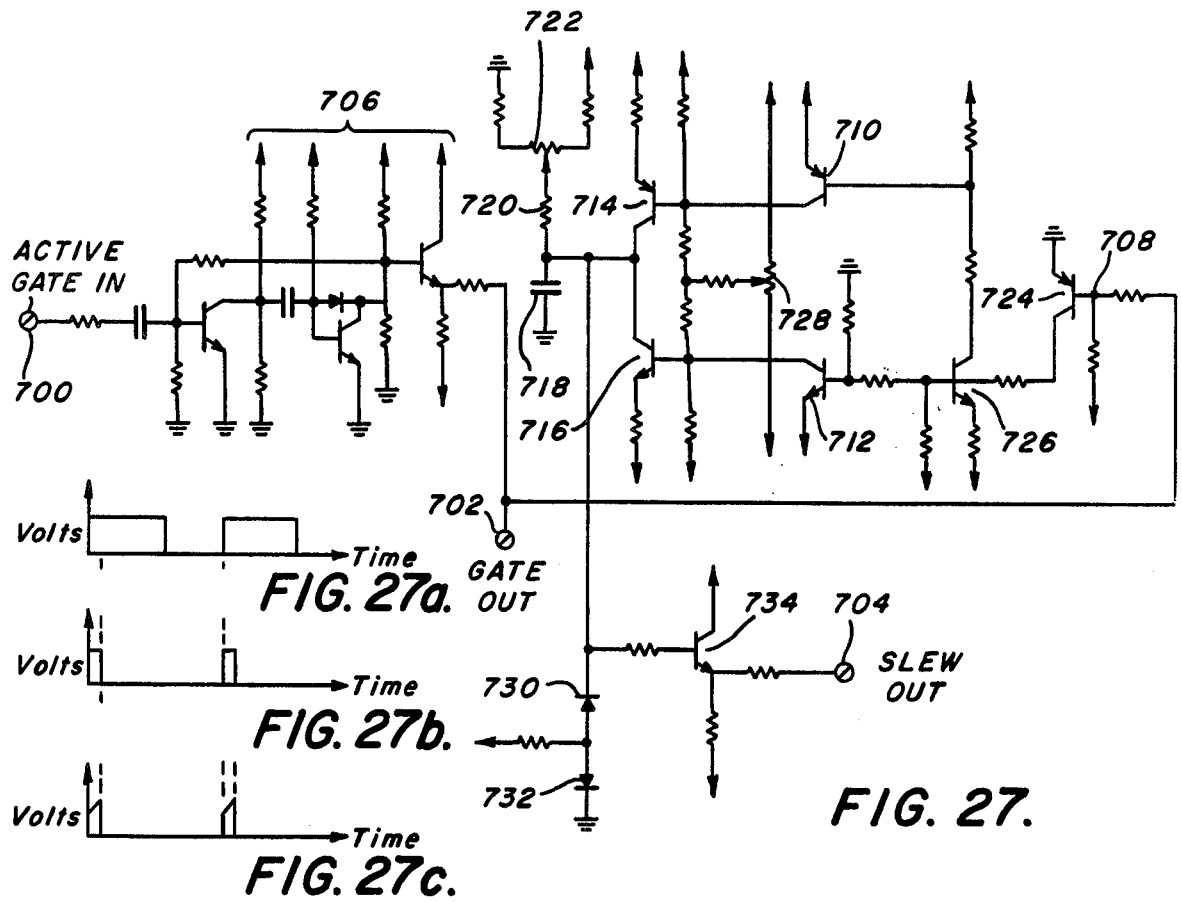
FIG. 27a.
FIG. 27b.
FIG. 27c.
FIG. 27.

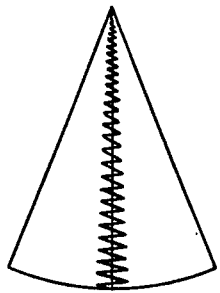
FIG. 54.
FIG. 55.
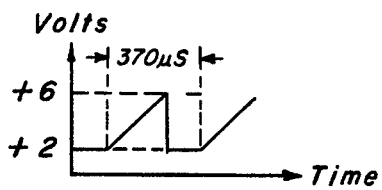
FIG. 56.
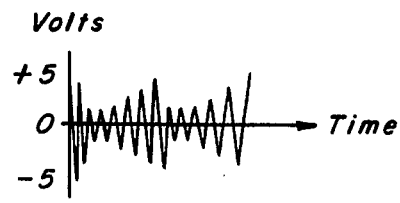
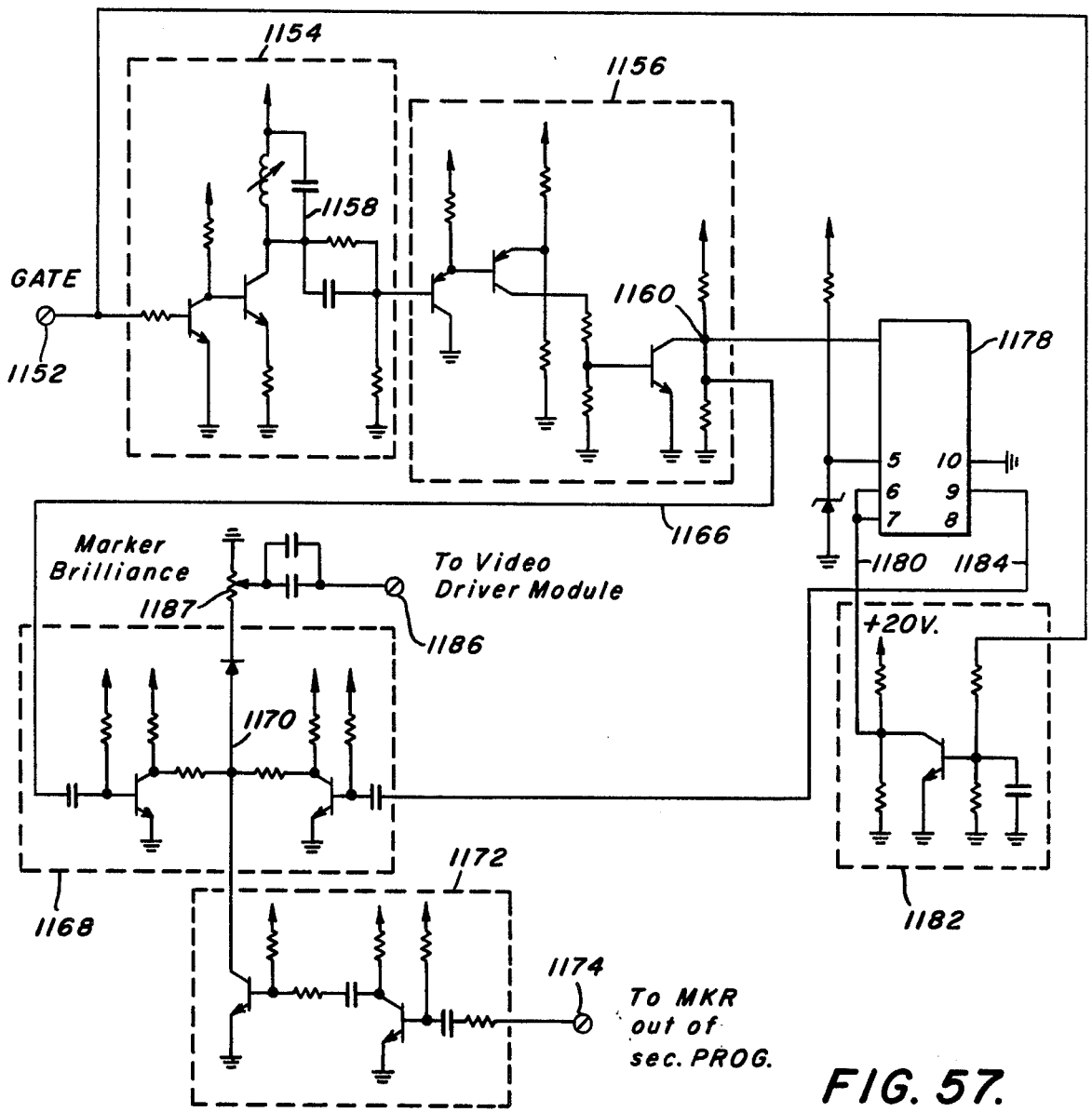
FIG. 57.

ULTRASONIC SCANNING APPARATUS

BACKGROUND OF THE INVENTION

1. Field of the Invention

This invention relates to ultrasonic scanning apparatus wherein an ultrasonic transducer is mounted for movement within a predetermined path with the motive force being provided by magnetic means, and, in a preferred form, it relates to such apparatus wherein servo-control is provided.

2. Description of the Prior Art

In general, the use of ultrasonics in testing of specimens has been widespread in many environments including medical diagnostic and therapeutic uses. In medical B-scan use, an insonifying transducer has been positioned in acoustically coupled relationship with a patient or specimen, and the transducer is moved along a linear path with transverse oscillation or rocking of the transducer during such linear movement serving to provide a "sector scan." It has been known to effect such transducer movement by manual manipulation in respect of both linear and angular scanning motions. Such an approach has its limitations as such a procedure is quite sensitive to operator skill. For example, one operator may scan the probe across the subject or workpiece much faster than another, and thus obtain a darker, more sparsely scanned image. As both grey-level renditions and resolution capabilities are extremely important to the amount of information and reliability of information produced by the ultrasonic scanning procedure, it is highly undesirable to have the results so heavily dependent upon operator skill. As a result, efforts have been made to avoid reliance upon the operator's skill in manual manipulation of the transducer.

U.S. Pat. No. 3,690,311 discloses an attempt to provide compensation for variations in operator dependent scanning systems by adjusting the pulse repetition rates accordingly in order to attempt to establish an improved, more uniform display.

It has previously been suggested to provide a wide range of mechanical means for moving an ultrasonic transducer so as to eliminate the need for heavy dependence upon manual manipulaton. U.S. Pat. No. 3,927,661 employs several versions of belt and pulley arrangements for establishing angular position changes in an ultrasonic transducer. The use of galvanometers as torque meters and mechanical belts is disclosed. In addition to the undesirable mechanical dependence, no feedback as to actual angular position is provided by the system disclosed in this patent.

U.S. Pat. No. 3,955,561 discloses gear means for moving a transducer, which is positioned within a housing, and means for determining the transducer position. There does not appear to be means for adjusting the position to correct for errors therein responsive to a direct representation of the angular transducer position. A similar system is disclosed in U.S. Pat. No. 3,974,826.

U.S. Pat. No. 3,784,805 discloses a transducer array which is rotated through direct coupling to a drive unit.

U.S. Pat. No. 3,765,229 discloses mechanical means for driving a pendulum which has a transducer mounted at the lower end of a pendulum arm and is adapted to inspect curved sheets which are immersed in a tank of liquid.

U.S. Pat. No. 3,406,564 discloses a mechanical drive for transducer movement. There is also disclosed a resolver which is said to indicate the position of the transducer during oscillation, but the details of the same are not disclosed. There is no indication as to any corrective action being taken in the event of departure of the signal from the desired position.

It has also been suggested to substitute for mechanical motion, whether manual or performed through equipment, an electronically switched array of stationary transducers. See, for example, U.S. Pat. No. 3,789,833. As is noted in this disclosure, there is the need to simulate both translational and angular rocking motion of a transducer probe in such an array. This disclosure provides multiple arrays in which three linear arrays of transducers are sequentially scanned with each array scanning along different search angles. One severely restrictive obstacle to adoption of such an approach is the requirement for the extremely large number of transducers and electronic circuits needed to simulate a reasonably large number of manual search traverses and angles, such as is commonly executed by a physican during an ultrasonic tomogram manual scan procedure.

It has also been known to provide real-time phased-array sector scanners which employ rectangular transducer surfaces which have been serrated into an array of bar-shaped transducer elements. Electrical signals delivered into these transducer elements and recovered signal echoes from the specimen are individually processed by a plurality of circuits under digital control. Time-varying time-shifts of addition of return signals simulates electronically the effect of oscillating or wobbulating the transducer surface on the specimen. A visual display on a cathode-ray tube monitor is frequently provided. While the motivation for such an electronic approach has been the inefficiency of some of the mechanical substitutes for manual transducer manipulation, these electronic systems also have shortcomings. First of all, the reliance upon digital time-shifting circuitry to simulate transducer oscillation is cumbersome and expensive, as well as adding to the complexity of the system. Another limitation is the speed limitation with which the radio frequency transducer signals can be converted into and processed digitally.

There remains, therefore, a need for an ultrasonic scanning system which provides an effective substitute for manual movement of a transducer through a linear and/or rocking or wobbulating pattern. There remains the further need for such a system wherein means are provided for not only effectively controlling the movement of the transducer in a predetermined path, but through servo-control, also confirming the accuracy of such movement and providing means for compensating for any departure from the desired position should such a departure occur.

SUMMARY OF THE INVENTION

The present invention has solved the above-described problems by providing a housed, ultrasonic transducer adapted to be moved in a predetermined path by magnetic means. Electrical means are provided for energizing the transducer and receiving signals therefrom. The magnetic means may include both permanent magnet means and electromagnet means with the electrical means serving to energize the electromagnetic means.

Position sensing means may be provided for determining the position of the transducer within the predetermined path. Signal processing means for comparing a signal from the position sensing means with a signal representative of the desired position and emitting a position correcting signal if a difference between the actual and desired position exists. In a preferred embodiment of the invention, the transducer is rotated about an axis which passes through the transducer assembly. In another preferred embodiment of the invention, the transducer is pendulum mounted.

It is an object of this invention to provide a reliable, precisely controlled system for effecting transducer movement in a rocking or oscillating mode through a predetermined path.

It is another object of the present invention to provide such a scanner wherein sensing means will monitor the actual position of the transducer.

It is another object of the invention to provide such a system wherein signal processing means will serve to emit corrective signals when the position of the transducer departs from the desired position.

It is a further object of this invention to provide such a scanner which employs magnetic drive means to effect movement of the transducer through the predetermined path.

It is another object of this invention to provide a servo-controlled ultrasonic scanning apparatus wherein the movable mechanical elements are low in inertia.

It is a further object of this invention to provide an ultrasonic scanner of the above-described type which is adapted for economical manufacture and durability.

It is yet another object of this invention to provide a real-time ultrasonic scanner adapted for visual readout.

These and other objects of the invention will be more fully understood from the following description of the invention on reference to the illustrations appended hereto.

BRIEF DESCRIPTION OF THE DRAWINGS

FIG. 1 is a schematic front elevational view showing a portion of one embodiment of a scanner of this invention.

FIG. 2 is a schematic right-side elevation of the scanner shown in FIG. 1.

FIG. 3 is a cross-sectional illustration of the scanner portion shown in FIG. 2 taken through 3—3.

FIG. 4 is a schematic elevational view of a scanner portion similar to that of FIG. 1, but showing a modified coil construction.

FIG. 5 is a schematic illustration of an alternate form of magnetic member.

FIG. 6 is a schematic illustration of one embodiment of the ultrasonic scanner shown in a sealed housing.

FIG. 7 illustrates schematically a form of position sensing means contemplated by one embodiment of this invention.

FIG. 8 is a schematic top plan view of the position sensing means shown in FIG. 7.

FIG. 9 is a schematic illustration of another embodiment of position sensing means.

FIG. 9(a) is a top plan view of the position sensing means of FIG. 9.

FIG. 10 is a schematic cross-sectional illustration of another embodiment of the ultrasonic scanner of this invention.

FIG. 11 is a schematic partial illustration of the ultrasonic scanner of FIG. 10 taken through 11—11 of FIG. 10.

FIG. 12 is a schematic illustration of another embodiment of the scanner of the present invention.

FIG. 26 illustrates a circuit for a form of sectoring programmer usable in the present invention.

FIG. 27 illustrates a circuit for a form of chirp programmer usable in the present invention.

FIGS. 27(a), 27(b) and 27(c) illustrate voltage versus time plots associated with the chirp programmer.

FIG. 54 illustrates schematically a form of sector presentation.

FIGS. 55 and 56 illustrate voltage versus time plots of signals being processed by the equipment of the present invention.

FIG. 57 illustrates a circuit for a form of marker generator suitable for use in the present invention.

DESCRIPTION OF THE PREFERRED EMBODIMENTS

Figure 13:
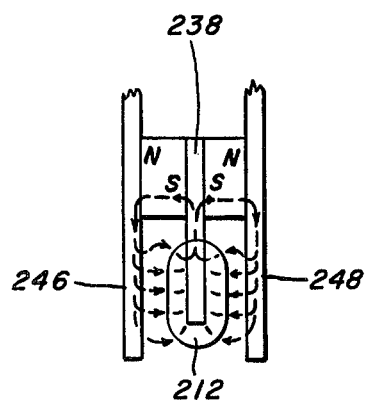
FIG. 13 is a fragmentary schematic view of a portion of the scanner embodiment shown in FIG. 12.
Figure 14:
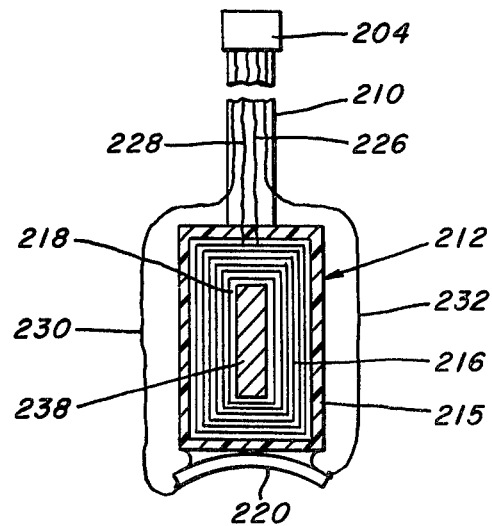
FIG. 14 shows a cross-sectional view of the driving coil and permanent magnet rail taken through 14—14 of FIG. 12.

As used herein, the expressions "test specimen" or "specimen" will refer to various types of specimens to be tested by ultrasonic B-scan or through scan, including medical tests performed directly on a patient or portions of a human or animal body which are being tested ultrasonically or treated ultrasonically, as for therapeutic purposes. While, for purposes of clarity of description, specific reference will be made to use of the ultrasonic scanner of this invention in medical environments, it will be appreciated that other forms of test specimens may be subjected to testing or treatment by the apparatus of this invention in addition to the preferred medical uses, and such other uses are expressly contemplated.

Referring now more specifically to FIGS. 1-3, there is shown the transducer assembly and drive means of one embodiment of the present invention. A focused transducer 2 is secured to a permanent magnet 4 by means of a suitable adhesive (not shown) such as a silicone cement or other suitable means in order to establish a transducer assembly. A pair of needle bearings 8, 10 project outwardly in a generally radial direction from the transducer assembly. In the form shown, the needle bearings 8, 10 are secured to the permanent magnet 4 and are disposed in generally diametrically opposed position. Support means 12, 14 which, in the form shown, consist of a pair of electrically conductive leaf spring members have an upper portion secured to the housing (not shown in this view) and a lower depending leg portion in retentive and electrically conductive contact with the needle bearings 8, 10. It will be appreciated that the support means 12, 14 should serve as leaf springs so as to firmly engage needle bearings 8, 10 for purposes of both mechanical support of the permanent magnet-transducer assembly and effective electrical conductive efficiency therethrough. It will be appreciated that the transducer 2 so mounted is adapted to rotate about an axis defined by the needle bearings 8, 10 upon application of a suitable driving torque as 15 indicated by the arrows in FIG. 1.

Referring now more specifically to the drive means, it is noted that a pair of magnetic armature poles 20, 22 have a pair of servo drive coils 24, 26 secured respectively thereto. Coil 24 is energized through a pair of electrical leads 32, and coil 26 is energized though electrical leads 34, in a fashion to be described below. The armature poles 20, 22 may be secured to the housing (not shown in this view) in any convenient fashion.

It will be appreciated that as the armature poles 20, 22 are energized through coil means 24, 26, respectively, the poles assume a given polarity. In the form shown in FIG. 1, pole 20 becomes a South pole, and pole 22 becomes a North pole. The interaction of the magnetic fields emerging from these electromagnets with the magnetic fields of the permanent magnet 4 causes forces to be applied to the permanent magnets in order to establish rotation of the permanent magnet-transducer assembly about the axis of needle bearings 8, 10.

When electrical current of either polarity is applied through drive coils 24, 26, or torque occurs on permanent magnet 4 and transducer 2. The torque will be proportional to the rotational acceleration of the permanent magnet-transducer assembly. The rotational velocity of the permanent magnet-transducer assembly will be proportional to the first definite time integral of the rotational acceleration. The angular position, therefore, becomes proportional to the second definite time integral of the rotational acceleration. As a result, the angular position is mathematically related to the initial currents imposed upon coils 24, 26 in a precise fashion. The relationship may be illustrated by the following formulae:

$$v = \int_{T_1}^{T_2} a\,dt - v_o \qquad (1)$$

$$x = \int_{T_1}^{T_2} v\,dt - x_o \qquad (2)$$

wherein
$T_1$ is the initial time
$T_2$ is the final time
$a$ is the acceleration of the transducer
$v$ is the velocity of the transducer
$v_o$ is the initial velocity of the transducer
$x$ is the position of the transducer
$x_o$ is the initial position of the transducer Current is provided to coils 24, 26 not only to provide the prime moving force for rotation of the permanent magnet-transducer assembly, but also, in a fashion which will be described below, to correct for departures from the desired, predetermined position of the transducer.

In this form of the invention, the permanent magnet 4 also functions as a dampener to dampen the acoustical behavior of the transducer.

Referring now to FIG. 4, there is shown a modified form of the system described in connection with FIGS. 1-3 in that in lieu of use of a pair of coils 24, 26, there has been provided a single coil 38 which is wrapped around the tubular magnetic member 45 and is energized through leads 40. A first armature pole 42 has a portion extending into coil 38, and a second armature pole 44 also has a portion extending into coil 38.

Referring now to FIG. 5, there is shown a modified form of electromagnet member which has an annular shape, is electrically coupled to the leads 40 and defines an opening 52.

Referring now to FIG. 6, there is shown a form of housing 58 which is suitable for use with the ultrasonic scanner of the present invention. In general, the housing may be considered as a sealed enclosure which permits electrical communication between the interior and exterior thereof. In the form shown, the housing 58 consists of a generally circular container bottom wall 60 and an annular sidewall 62 which cooperates with a closure 64. As is shown in FIG. 6, the upper portions of support means 12, 14 are secured to closure 64 by mechanical fasteners 66, which may conveniently be screws. The upper extremities of armature poles 20, 22 (not shown in this view) may also be secured to the closure 64 in similar fashion. In the form shown, the closure 64 is in sealed engagement with sidewall 62 by means of O-ring 72. Other means could be provided to sealingly close the upper portion of housing 58. The container bottom wall 60 will consist of an acoustically conductive material as it is through this wall that the ultrasonic waves will be emitted (and in B-scan embodiments received). In order to facilitate intimate acoustical contact with the specimen while preserving comfort, in those instances where a patient is involved, a compressible silicone base portion 74 is secured to the outer surface of bottom wall 60. The position of a specimen 76 is generally illustrated in FIG. 6. The housing will contain a suitable liquid (not shown) which is acoustically conductive and preferably either sterilized or antiseptic.

Continuing to refer to FIG. 6, it will be appreciated that it will be necessary to provide a source of electrical energy within the housing to energize the transducer 2 and to energize coils 24, 26, 38, as well as to transmit the electrical equivalent signals relating to the echoed sonic pulses returned to the transducer. One convenient and preferred means for accomplishing this is to permit electrical communication through the closure 64. An electrical cable 80 terminates in a female plug 82 which is adapted to cooperate with male plug 84 in effecting electrical communication between the ultrasonic scanner interior and housing exterior.

With regard to energizing the coils 26, 24, 38, one convenient means would be to employ electrically conductive fasteners to secure the upper portion of poles 20, 22, 42, 44 to the closure and to provide electrical leads connecting these fasteners to the appropriate portion of male plug 84. Similarly, the electrical signals for energizing the transducer and for transmitting the electrical equivalent of the echoed sonic pulses may be communicated through fasteners 66, through two leads (not shown) to male plug 84. In connection with this aspect of the electrical system, the present invention provides another unique feature. Electrical leads 88, 90 which are shown schematically in FIG. 6 and have been eliminated from FIGS. 1-3 for simplicity of illustration, serve to provide an electrically conductive path between the needle bearings 8, 10 and the transducer 2 without requiring the use of flexible wires at this point.

Referring now to FIGS. 10 and 11, another embodiment of the invention will be considered. In this embodiment of the invention, there is disclosed a form which is suitable for certain specialized test procedures, such as medical biopsy procedures, wherein there is need for medical equipment to pass through the scanning apparatus. As is shown in FIGS. 10 and 11, a housing 96 which may be generally similar to housing 58 is provided with a bottom wall 98, having an opening 100, a sidewall 102 and a tubular interior wall 104, which defines a bore 106, which passes completely through the housing 96. While the operative portions of the ultrasonic scanning apparatus may be generally similar to that discussed above, certain changes are made in order to accommodate generally centrally disposed bore 106. Transducer 110 and permanent magnet 112 are of annular configuration. Needle bearings 114, 116 engage support means 118, 120, and coil 122 energizes armature poles 124, 126. (If desired, two coils, such as in FIGS. 1-3, may be employed in lieu of coil 122.) The housing 96 is sealed and contains a suitable liquid 128 which is acoustically conductive and preferably either sterilized or antiseptic in nature. An annular closure 130 is sealingly positioned within the upper portion of the housing 96 with the seal being effected by O-rings 136, 138. Shown schematically in this view are the electrical means for communication between the interior and exterior of the sealed housing. In the form shown, a plug pin 142 is adapted to be received within female plug member 144 which is operatively associated with cable means 146. Sufficient electrical connections are provided in order to energize coil 122 and transducer 110 as well as receiving return electrical signals from transducer 110.

In the embodiment shown in FIGS. 10 and 11, the housing 96 may conveniently be machined or otherwise made from a suitable plastic which is sonically conductive, such as a solid acrylic plastic, so that lumen or bore 106 extends completely through housing 96. The magnetic armature poles 124, 126 perferably have annular extensions 148, 150 secured to the bobbin (not shown) upon which coil 122 is wound.

In use of the embodiment shown in FIGS. 10 and 11, the undersurface of bottom wall 98 is placed upon the specimen 152, which is shown in parallel spaced position for clarity of illustration. The instrument is turned on to permit proper identification of an organ, for example, such as a kidney, and a biopsy or aspiration needle device (not shown) is manually inserted into the bore or lumen 106 from upper extremity in order to enter the specimen 152. In addition, if desired, the visualized version of the data produced by this instrument, may be employed in order to guide depth of penetration of the needle device within the specimen.

While, in the form shown in FIGS. 10 and 11, the system employs openings which are coaxial with the central longitudinal axis of the housing, other positions for the openings may be provided, if desired. For example, the openings may be radially displaced from the central axis. They may also take the form of generally radially oriented slots disposed in circumferential discontinuities in the permanent magnet, the transducer and the housing, for example.

EXAMPLE I

In order to provide further guidance as to how one might manufacture the ultrasonic scanner of the present invention, an illustrative example of the materials which might be employed will be described. The housing may consist of a bottom wall of acoustically transparent material, such as 0.032 in. thick black rigid vinyl, and the sidewalls and closures consisting of machined brass. If desired, the bottom wall and sidewall of the housing need not be made as a unit. A tubular brass barrel may be closed at its lower extremity by a frontal plate secured thereto. Suitable coatings may be provided on the interior of the vinyl plate, such as an initial coating of silver paint, such as that sold under the trademark Polycomp Silver Paint, and a final coating of copper applied by electroplating with a solution consisting of cupric sulphate and dilute sulfuric acid. The acoustical-coupling liquid which is employed in the housing may be castor oil. The driving coils, such as coils 24, 26, 38, 122, may consist of about 400-800 turns of #36 type ML magnet wire. The transducer elements may consist of a ¾ in. diameter lead metaniobate transducer disc (such as that sold under the trademark R81 by Klramos, Inc. of Liston, Ind.) originally 0.063 in. thick ground to 0.028 in. thick and ground spherically at 15 centimeter focus.

The transducer may be electroplated with cupric sulphate and sulfuric acid. The adhesive employed to secure the transducer to the permanent magnet may be any suitable acoustically conductive material which will provide the integrity of bond desired. A suitable material would be a mixture of a 1:1 by volume of General Electric Clear Silicone Glue and Seal and 50 micron tungsten granules. The tungsten serves to provide damping of the transducer. The permanent magnet may consist of a machinable ceramic magnet, such as one composed of ferrite. A suitable specific one is that marketed under the trade designation Ferrofluoidics. The needle bearings may conveniently be made of copper wire. A suitable housing for the driving coils, 24, 26, 38, 122 may consist of two machined 0.032 in. thick, black, rigid vinyl shoes, which may have slots on opposite sides to receive coil wraps. The fasteners may conveniently be 2-56, 6-32 brass machined screws. Alternatively, for the electrical communication between the exterior of the sealed housing and the interior, a "Jones-Plug" and socket convention combination may be employed.

Referring now to FIGS. 7 and 8, one form of transducer position sensing means will be considered. As is shown in this view, the transducer 158 is secured to an overlying permanent magnet 160 and is adapted to be moved along a predetermined oscillating path about the axes of needle bearings 162, 166. A vane element 168 is secured to the upper surface 164 of permanent magnet 160 and is oriented generally perpendicularly with respect thereto. In the form shown, the vane element 168 has a generally triangular configuration. A lamp 174, or other light source, is suitably energized by means not shown. A phototransistor 176 (such as that sold under the trademark "Fairchild FPT-100") which has a number of electrical leads 178 is positioned in spaced relationship with respect to light source 174. As the transducer 158 rotates about the needle bearing axis, the vane 168 will tend to permit different quantities of light to impinge upon phototransistor 176, thereby creating a situation wherein the total illumination received by the phototransistor 176 corresponds with the actual angular position of the transducer. This illumination is converted by the transistor 176 to electrical signals which will be processed as hereinafter described to provide a specific indication as to the transducer's actual position.

Referring now to FIGS. 9 and 9(a) is another preferred form of transducer position sensing means. In this embodiment fixed electrical sensing coils 188, 190 are positioned in surrounding relationship, respectively, to eddy current vanes 192, 194. These vanes are mounted upon permanent magnet 186, which has secured thereto transducer 184. The transducer is adapted for oscillating movement about needle bearings 196, 198. As the vanes 192, 194 will move with the transducer-permanent magnet assembly as it rotates, and the coils 188, 190 are mounted in a stationary position (by any conventional means, not shown), the inductance of the coils 188, 190 will become related to the angular position of the transducer 2. The vanes 192, 194 are oriented so as to be mutually opposing. While a single vane and coil might be employed, there are advantages to the use of at least two such vane and coil combinations. When both vanes 192, 194 are oriented in opposing position and energized by radio frequency currents, connection to the differential position-detection circuitry (which is know to those skilled in the art) results in a DC output voltage which is proportional to the angular position of the transducer. The opposition principle works with the circuitry to obtain improvements in linearity of read-out superior to a single coil system.

EXAMPLE II

As an example of how the vane coil sensing system may be employed, please consider the following. The vane elements may be made from 0.020 in. thick aluminum sheet and secured to the permanent magnet by any suitable adhesive, such as that sold by General Electric under the designation Clear Silicone Glue and Seal. The sensing coil housing may be made from machined, 1 in. diameter case Lucite rod. Radio frequencies ranging from 0.2 to 5.0 milliamps at frequencies ranging from 0.2 to 2.5 MHz may be employed. Typical inductance ranges fall within the range of +0.0 to −20.0%. The coils should be operated in tone bursts suitably gated so as to minimize interference with receipt of acoustical pulses from the transducer 184.

Referring now to FIGS. 12–15, another embodiment of the ultrasonic scanner of the present invention will be considered. There is shown a sealed housing 200 having a plug 202 for permitting electrical communication between the interior and the exterior of the sealed housing. A pivotally mounted bearing block 204 is secured within the housing and has a substantially rigid column member 210 depending therefrom. Secured to a lower portion of column 210 is a coil assembly 212 which consists of a coil support member 215 which receives the coil wiring 216 and defines a coil opening 218. Secured to the lower end of the coil assembly 212 is a focused transducer 220. (The cement securing the transducer 220 to the coil assembly 212 preferably includes a tungsten powder which serves to act as the backing for the transducer 220.) Electrical leads 226, 228 serve to energize the coil 216. Electrical leads 230, 232 serve to energize transducer 220 and to provide for communication of the electrical signal related to reflected sonic energy received by the transducer 220. The electrical leads 226, 228, 230, 232 are preferably secured to exterior of column 210 and are electrically connected, either directly as by flexible wires or through bearings in block 204 with housing plugs 202. A curved magnetic central pole 238, which, in the form shown, is of generally rectangular cross section, is received within the opening 218 of the coil assembly 212 so as to permit relative movement therebetween as the transducer 220 is moved along its predetermined path as defined by the magnetic central pole 238. Arrays of permanent magnets 240, 242 are positioned at opposed sides of magnetic central pole 238.

In operation, the coil 216 is energized through electrical leads 226, 228 to establish a magnetic field which, as a result of positioning of the coil 216 with respect to permanent magnets 238, establishes movement of the transducer bearing coil assembly 212 along the magnetic central pole 238. As the coil assembly 212 approaches either array of permanent magnets 240, 242, the position sensing means (to be described below) provides signals to reverse the direction of movement of the coil assembly 212 along the magnetic central pole 238.

As is shown in FIG. 13, in a preferred form of the invention, the housing may contribute to magnetic efficiency of the scanner. By providing a magnetic front wall 246 and a magnetic rear wall 248, a return path is provided for the magnetic field for magnetic central pole 238.

EXAMPLE III

The following provides an example as to how the housing may serve as a portion of the magnetic path. In order to obtain large motor torque to oscillate transducer 220 along the arc defined by central magnetic core 238 (which may conveniently be about a 3 to 4 inch path measured along the arc) within about 50 to 100 milliseconds, one should attempt to bias coil 216 into a large DC magnetic field. If the casing walls 246, 248 are magnetic and of sufficient thickness, (i.e. on the order of 0.05 inch to 0.15 inch) such as to support 3000 gauss of flux, for example, the casing may serve to provide the return path for the magnetic central pole 238. Permanent magnet assemblies 240, 242 provide the magnetic biasing throughout the length of magnetic central pole 238. Magnetic gaps may be kept short and on the order of about ¼ inch. This results in a high energy magnetic structure. The permanent array 240, 242 serves to provide the magnetic bias field to produce transducer movement when coil 216 is energized.

As a result of the design of this embodiment, it is possible to effect large values of reversible, angular acceleration. The moving inertia is limited primarily by the drive coil assembly 212, the transducer 220, the support column 210 and the bearing block 204. However, the dominant factors are the coil assembly 212 and transducer 220 as in circular geometry, the moment of inertia is proportional to the square of the radius of the mass from the bearing block 204, and only the largest radius, e.g. that of the transducer 220 and coil 216, contributes heavily. As a result of the present design, it is possible to make the entire moving assembly (the coil assembly 212, the transducer 220, the column 210 and the bearing block 204) of a very light weight. For example, it may have a total weight of under about 20 gms. This relatively low moving mass permits the resultant high acceleration. The lower region of the pendulum may, as a result, oscillate through the arc defined by magnetic central pole at rates in excess of 10 swept scans per second or 5 complete cycles per second.

While the entire housing 200 could be filled with a suitable acoustically conductive liquid, it is preferred to fill only the lower regions of the housing to a level above the transducer 220. In this fashion, the liquid does not serve to dampen the movement of the transducer bearing coil assembly 212, and yet the liquid coupling to the lower wall 250 of the housing is provided,. Among the preferred materials for such use is an absolute ethyl alcohol of 200 proof as this has a relatively low viscosity and high resistivity while preserving desired antiseptic characteristics in the event the housing were to leak. An alternate means to the use of acoustically conductive liquid would be to provide a series of permanent magnetic elements of alternate polarization, such as those indicated generally by the designation 256, which may be either positioned on the upper surface of lower housing wall 250 or therewithin. These magnetic elements may conveniently be magnetic rubber elements. These magnets could serve to capture ferrofluids. The magnetic elements 256 will capture the ferrofluids, but would not interfere with the sonic coupling between transducer 220 and the test specimen (not shown in this view).

Figure 15:
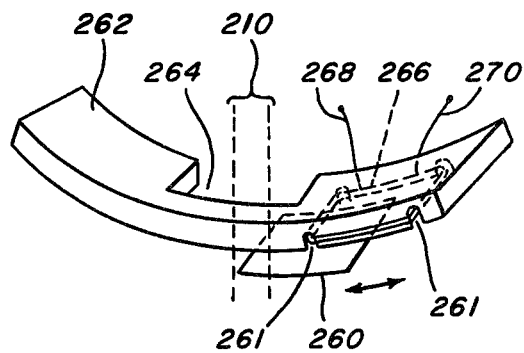
FIG. 15 shows a schematic perspective of the position sensing means of FIG. 12.

A preferred form of transducer position sensing means has been incorporated into this embodiment. Referring to FIGS. 12 and 15, a vane element 260, which may consist of a sheet of material, is secured in a position generally perpendicular to the column 210 and is oriented generally parallel to the magnetic central pole 238. A curved coil support 262 defines a recess 264 which receives the column 210 and is positioned in spaced, overlying relationship with respect to vane 260. A position sensing coil 266 is mounted on the coil support. Electrical leads 268, 270 serve to provide electrical means for communication between housing plug 202 and positioning sensing coil 266 to energize the same. It will be appreciated that as the column moves during pendulum oscillation, the vane 260 will alter the inductance of coil 266 in linear proportion to the arcuate motion of transducer 220 along the path defined by magnetic central pole 238. If desired, the efficiency of the position sensing means could be improved through the use of two coils and two vanes positioned on opposite sides of recess 264 for the reasons noted above in connection with the discussion of FIGS. 9 and 9(a).

Figure 16:
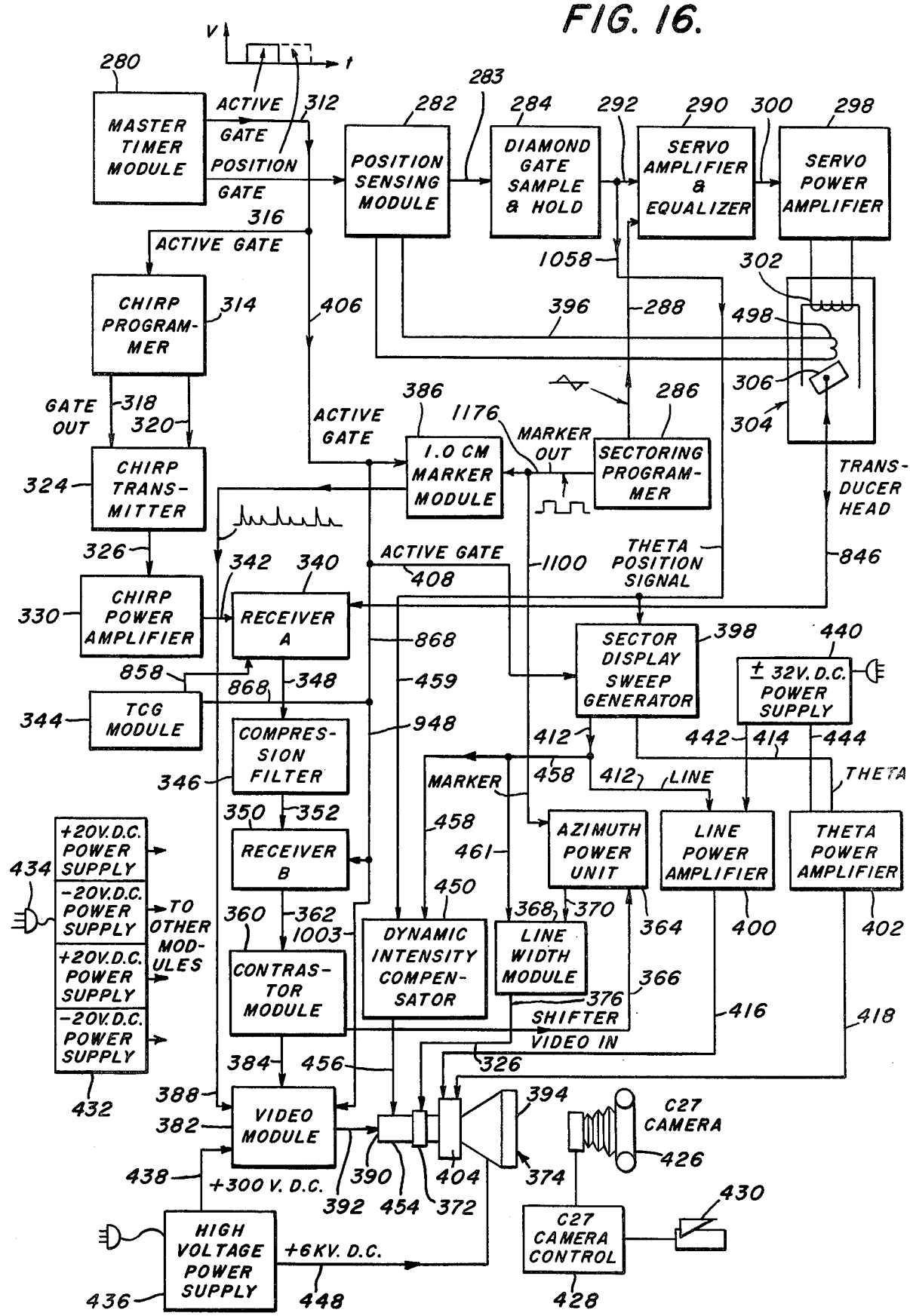
FIG. 16 is a block diagram showing one form of electrical control means of the present invention.

FIG. 16 illustrates a block diagram of a preferred form of signal processing means of the present invention. Master timer module 280 delivers two types of gate pulses. The first gate pulse is an "active gate" pulse, and the second gate pulse is a position sensing gate pulse. In order to provide more specific guidance as to an example of how the signal processing means may be employed, specific numbers will be used at certain portions of this description to describe timing and other capabilities of the system, for purposes of example only, and such numbers are not to be deemed limiting of the invention, unless the context expressly indicates to the contrary. The active gate pulse and position sensing gate pulse may repeat every 370 microseconds, for example. The active gate pulse determines the time (typically about 260 microseconds, for example) starting from the initiation of the transmitted transducer wave or chirp and including the waiting period during which reverberations return, from within the test specimen. The position sensing gate pulse, which may typically be about 80 microseconds, for example, occurs after the active gate pulse shuts off and enables the position sensing circuitry to obtain a reading of angular transducer position without interfering with the sensitive receiver functions.

In general, the signal processing means may be considered as consisting of means for providing a signal to the electromagnetic means for effecting regular movement of the transducer in its predetermined path and means for sensing the position of the transducer and correcting such movement when a departure from the predetermined angular movement is detected. This latter means consists of means for actually determining the position of the transducer and comparing this actual position with the signal for the desired position. In addition, the electrical means provides electrical signals to energize the transducer and returned signals representative of the specimen reflected acoustical waves. Means are provided for converting the reflected signals in the form of electrical voltages into desired forms of readout, such as the video display, which is disclosed in the preferred form of the invention.

In general, the sectoring programmer 286 provides an output in the form of a triangular waveform over line 288. This results in reciprocating movement of the transducer 306 along its angular path. During the ramp portion of the triangular wave, the transducer is moved in a first direction, and during the voltage drop portion of the waveform, the transducer moves in the opposite direction.

In general, the master timer module 280 delivers two types of gate pulses. The first type of gate pulse is the "active" gate, and the second is the "position" gate. This pair of pulses repeats, for example, every 370 microseconds. The active gate pulse determines the time period (typically 260 microseconds, for example) between initiation of the transmitted chirp and the waiting period during which reverberations return to the transducer 306 from within the test specimen. The position gate, which, typically, is about 80 microseconds, for example, occurs after the active gate shuts off and enables the position sensing means to take a reading of angular transducer position without interfering with the sensitive receiver functions. In other words, the system which controls transducer emissions and receipt of reflections is maintained independent in respect of time from the position sensing and error correction systems.

The position sensing module 282 is activated only during the period the position gate signal is in an "on" state. During the "on" time, a reading of angular transducer position is taken by means of sensor coil 498 and an analog voltage becomes available from the position sensing module 282 only during the position gate "on" time.

The diamond gate sample and hold module 284 receives over lead 283 only those voltage outputs from position sensing module 282 emitted during the position gate "on" time and averages between signals received therefrom so as to provide a smoothly varying voltage that represents the transducer's actual angular position.

The sectoring programmer 286 produces a triangular waveform which may be about 6.0 volts peak-to-peak, for example, and range from about 5 to 13 Hz. This triangular waveform serves as the main control over the transducer movement and position in comparison with the signal emitted by the diamond gate sample and hold 284 which serves to impose a corrective factor. The triangular waveform passes by means of line 288 to the servo amplifier and equalizer 290. The servo amplifier and equalizer 290 compares the signal received from the sectoring programmer 286 over lead 288 with the actual position related signal received from diamond gate sample and hold 284 over lead 292. The difference between these two signals which represents the magnitude of departure of the actual transducer position from the desired transducer position as indicated by the sectoring programmer 286 is amplified and fed into servo power amplifier 298 on line 300 which, in turn, feeds current into the drive coil 302 of the scanner assembly 304 to drive transducer 306.

With respect to energizing the transducer 306 electrically and receiving return signals therefrom, the active gate signal emitted by the master timer module 280 proceeds through the chirp programmer 314, chirp transmitter 324, chirp power amplifier 330 and receiver 340 to transducer 306 in a fashion which will be described hereinafter. The reflected acoustical signals returning to the transducer 306 are returned to receiver 340 by means of lead 846. The details of this processing will be described hereinafter. The signal returned from the transducer 306 to receiver 340 is subsequently processed in order to ultimately be displayed on cathode-ray tube assembly 374.

The active gate signal passes by means of lines 312 and 316 to chirp programmer 314. This active gate signal serves to initiate the gate out signal from the chirp programmer 314 on line 318, and the slew out signal on line 320 from chirp programmer 314. These two signals enter chirp transmitter 324 and determine the length and frequency variation (shape) of the chirp waveform which is fed from the chirp transmitter 324 along line 326 to chirp power amplifier 330.

The amplified transmitted chirp is applied to receiver 340 through lead 342, rather than directly to the transducer head 306 because receiver 340 contains transmit-receive (TR) circuitry. Such transmit-receive circuitry isolates (disconnects) the chirp power amplifier 330 from the transducer 306 during the time that reverberations are received by receiver 340. Time-controlled gain module 344 increases receiver gain for feeble reverberations in proportion to the waiting time after the chirp. Compression filter 346 receives the output of receiver 340 over lead 348 and performs an analysis on each reverberation from the patient. After the chirp waveform is transmitted acoustically into the patient, many chirp waveform reverberations are simultaneously received, and this means that reflections from each anatomic part of the patient overlap in a very confusing manner. The compression filter 346 eliminates the overlap and sharpens the axial (depth) resolution. Receiver 350 receives the output of compression filter 346 by means of lead 352 and contains the conventional circuitry that converts the radio frequency mode to the A-mode signal and performs the "reject" function which prevents very small amplitude reverberations from appearing in the ultimate ultrasonic image.

Contrastor module 360 receives the output of receiver 350 over lead 362 and determines three types of video display contrasts. The first type of contrast is the normal grey-level contrast of the type one is used to adjusting on a television set. The second type of contrast is an axial edge enhancement which sharpens the resolution vertically in the displayed image. This enhancement is done internally within the contrastor module 360. The third type of contrast is the azimuthal edge enhancement, which increases resolution horizontally in the displayed image. The control function for the azimuth edge enhancement is present in the contrastor module 360, but the actual performance of the azimuthal edge enhancement is performed in the azimuth power unit 364, which receives the output of contrastor module over lead 366. The output of the azimuth power unit 364 serves to drive the secondary yoke 372 of cathode-ray tube 374 indirectly by passing of the output of azimuth power unit 364 through line width module 368 by means of lead 370 and lead 376.

The line width module 368 provides a controlled amount of horizontal astigmatism in each scanning line of the sector display, in order that as the lines become "more spread out" at the bottom of the sector, such lines also become "fatter" in proportion to the distance along the scan, in a direction towards the bottom of the display image. This "wedging" action improves the grey-level continuity without sacrificing resolution in the vertical axial direction in the displayed image.

The video module 382 receives both the imaging information from contrastor module 360 over lead 384 and the one centimeter dot-marker signals from the marker module 386 over lead 388. The combination of both the image and the marker are delivered to the grid control 390 of the cathode-ray tube assembly 374 by lead 392. The video module 382 provides the necessary master contrast, brightness and focus controls to provide the properly adjusted display on the cathode-ray tube as is commonly done in television.

The active gate signal which is emitted by master timer module 280 over lead 312, and the theta position signal which is emitted by position sensing module 282 over lead 396 enable the sector display sweep generator 398 to provide suitable sawtooth deflection signals, that, when amplified by the line power amplifier 400 and the theta power amplifier 402, power the main yoke 404 of the cathode-ray tube 374 to produce the sector format scanning raster. The active gate signal is introduced in the sector display sweep generator 398 by means of leads 312, 406 amd 408. The output of sector sweep generator 398 is introduced into line power amplifier by means of lead 412 and into theta power amplifier 402 by means of lead 414. The output signal of line power amplifier 400 is introduced into main yoke 404 of cathode-ray tube 374 by means of lead 416, and the theta power amplifier 402 output is introduced into main yoke 404 of cathode-ray tube 374 by means of lead 418.

As a means of providing a permanent record of the display of the cathode-ray tube assembly 374, there is shown a camera 426 which, in the form shown, is provided with a camera control 428, which may conveniently be that sold by Tektronix under the designnation "C27." Camera control 428 in turn is adapted to be operated by means of switch 430 which may conveniently be a foot switch. The camera setup may be such that the camera control module 428 receives a trigger signal from the switch 430 and produces a current pulse of a duration which is independent of the length of the time the switch 430 is operated. Such current pulse operates the electronic shutter of the camera 426. The pulse length is programmable at the camera control 428 in order that the exposure timing can be set to match the film and the f-stop being used. For example, one may employ about 0.2 seconds exposure of Polaroid Type 107 film with an $f/3.5$ setting.

A suitable regulated power supply assembly 432 of any conventional variety may be employed and is to be coupled through plug 434 to a suitable source of electrical energy and, in turn, is adapted to be electrically coupled to all modules which require energization. As the power supplies may be conventional, and the types appropriate will be readily apparent to those skilled in the art, further disclosure of these items need not be provided.

A high voltage power supply 436 which is connected by means of lead 438 to video module 383 and by means of lead 448 to cathode-ray tube assembly 374 is also illustrated in FIG. 16. A 32-volt regulated DC power supply assembly 440 has been shown being connected to line power amplifier 400 and theta power amplifier 402 by means of leads 442, 444, respectively. These power supplies 436, 440 also may consist of conventional forms of power supplies.

The dynamic intensity module 450 applies a control voltage through cathode-ray tube grid 454 by means of lead 456. This serves to increase the brightness of the display as the sector spreads from the top to the bottom of the display. This serves to resist the image being inherently brighter where it is "bunched up," i.e. at the top of the display screen 394. The line deflection signal controls these dynamic intensity changes by means of lead 458. The theta position signal is also applied (by way of lead 459) to dynamic intensity module 450 in order that the right and left edges of the raster are dimmed during the brief stopping of the transducer during reversal of its triangular scanning pattern. Otherwise, bright lines would appear during the slowing, oscillating velocity action of the transducer along its path along left and right edges of the displayed ultrasonic image on the cathode-ray tube assembly 374.

The line deflection signal (ramp waveform) which increases (modulates) the dithering waveform amplitude as the cathode-ray tube dot scans from top to bottom of screen 394 passes from sector display sweep generator 398 to line width module 368 by way of leads 412, 458 and 461. The lead 366 from contraster module 360 to azimuth power unit 364 provides a controlled amount of video signal to cause the azimuth power unit 364 to generate high currents (0.2 amperes, for example) which shift the dot on screen 394 horizontally.

Figure 17:
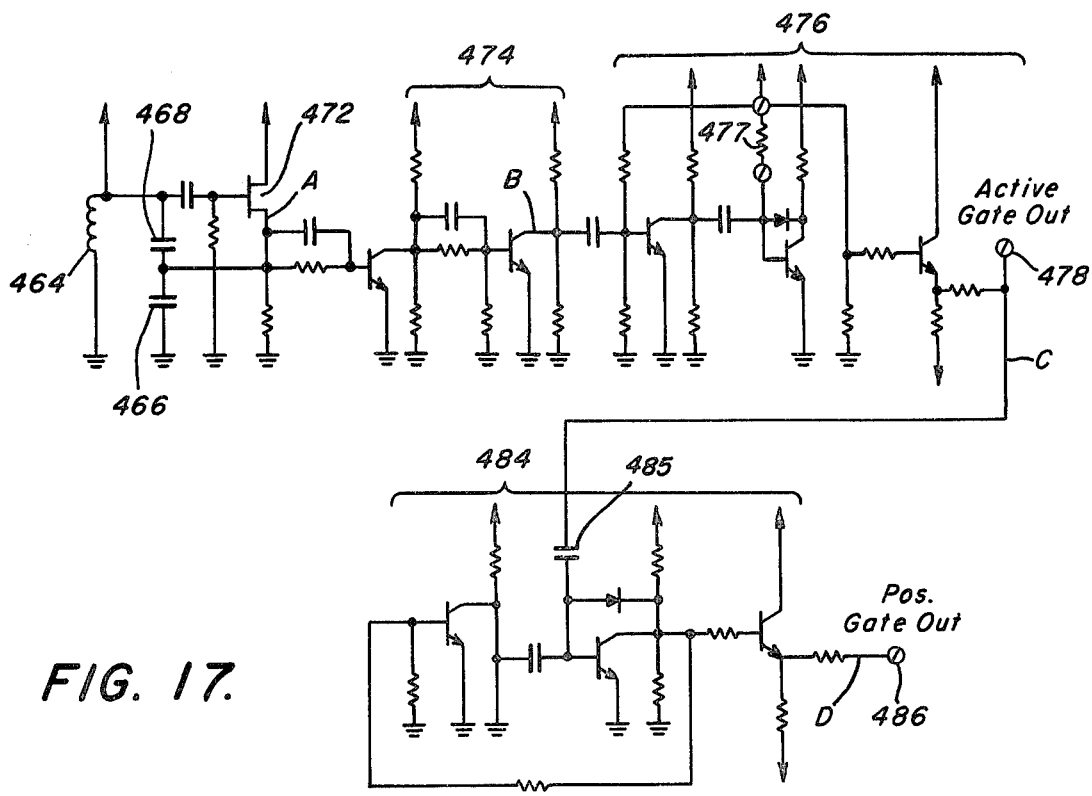
FIG. 17 shows a circuit diagram of a form of master timer module usable in the present invention.

Referring now to FIG. 17, wherein a specific form of preferred master timer module 280 is illustrated. The cycle time of operation of the master timer module is determined by inductor 464 and capacitors 466, 468. The field effect transistor 472 completes a Colpitts oscillator circuit that completes a period of sinusoidal oscillation every 370 microseconds, for example. Transistor circuit 474 convert the sine wave to a pulse waveform that activates one-shot multivibrator 476 to produce a rectangular pulse of 136, 200 or 266 microseconds, for example, once during each complete cycle period of the Colpitts oscillator operation. The active gate output 478 operates the active gate requirements of the ultrasound system, as well as initiating the second pulse from the position gate one-shot multivibrator 484, which provides the position gate output 486.

Figure 18:
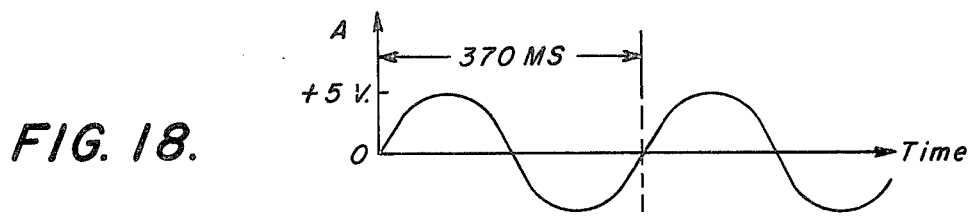
FIGS. 18 through 21 show voltage versus time plots of certain waveforms involved with the master timer module.
Figure 19:
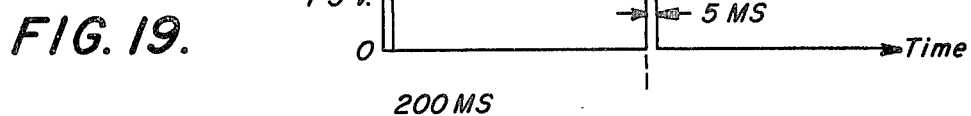
Figure 20:
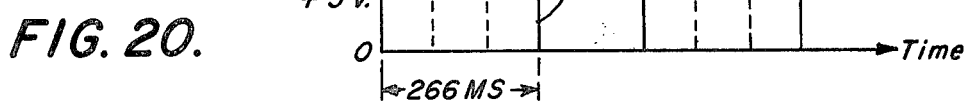
Figure 21:
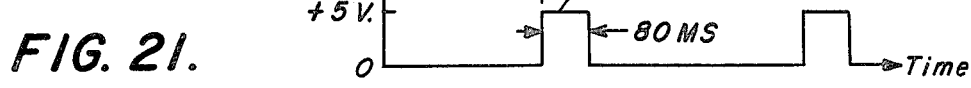

Referring now to FIGS. 18–21, the waveform involved in operation of the master timer module 280 as illustrated in the example provided in FIG. 17 will be considered. In FIG. 18 the sinusoidal oscillation produced by the Colpitts oscillator circuit is illustrated. It is noted that, in the form shown, the wave has a maximum amplitude of five volts, either positive or negative going, and a time cycle of 370 microseconds. In FIG. 19, there is shown the pulse waveform produced by transistor circuit 474. These pulses have an amplitude of +5 volts and occur every 370 microseconds. FIG. 20 illustrates the output of multivibrator 476 which is selectable at 136, 200 or 266 microseconds by changing the value of resistor 477. The trailing edge 479 of waveform 481 of multivibrator 484 initiates position gate pulse 483 of FIG. 21. Multivibrator 484 is triggered by capacitor 485 to produce position gate pulse 483. In this example, the reason the active gate times are changed is in order that the active times of 136, 200, 266 microseconds may correspond to a displayed sector image of 10, 15 and 20 centimeter depth in the test specimen, respectively. As a result, in this example, the system timing is changed to allow for three different magnifications in the displayed image.

Figure 22:
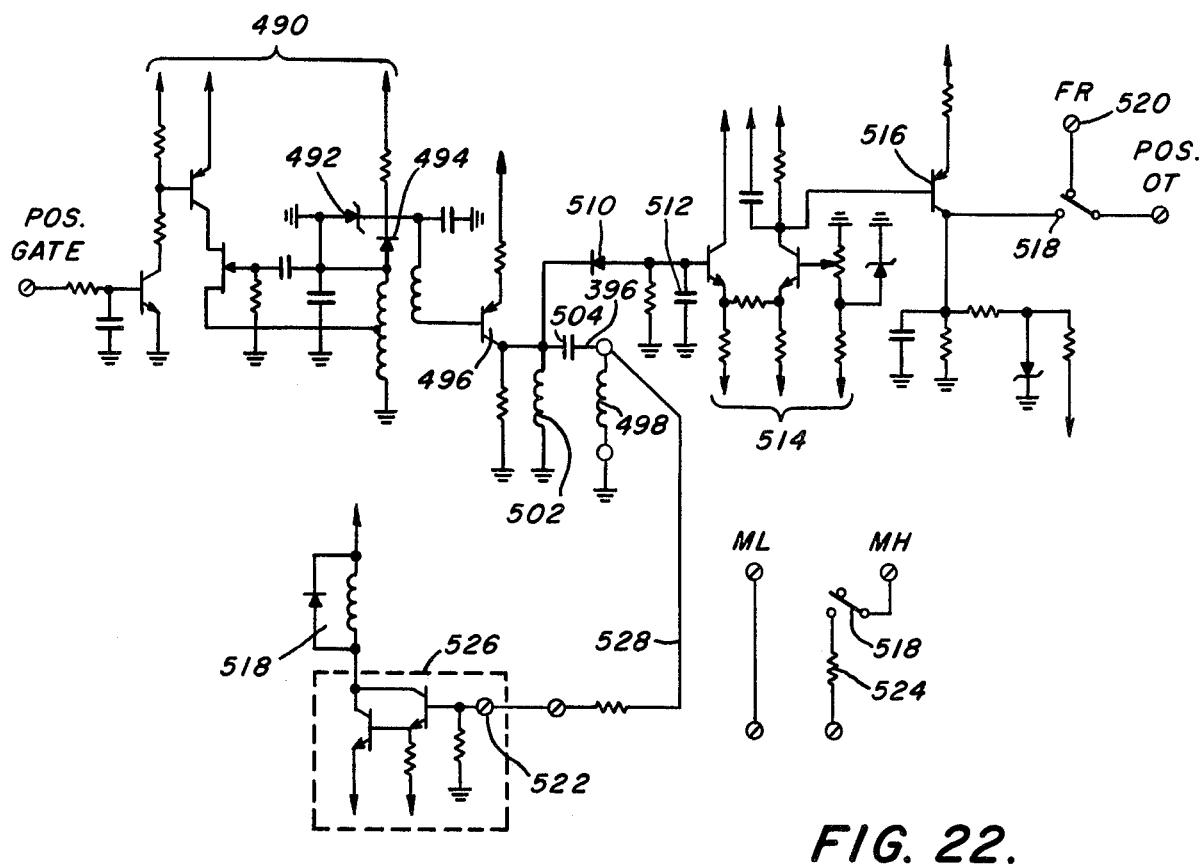
FIG. 22 illustrates a form of circuit usable for the position sensing module of the present invention.

Referring now to FIGS. 16 and 22, an example of a preferred form of position sensing module 282 will now be considered. The position gate signal emitted by master timer module 280 activates position sensing module 282 and such activation turns on the Hartley oscillator circuit 490, which, in turn, generates, for example, 10 volts peak-to-peak at 2.0 MHz during the "on" time of the position gate pulse. Diodes 492, 494 act in concert to limit accurately the amplitude of oscillation. Transistor 496 acts as a radio frequency current source which energizes the transducer head position sensing coil 498 through lead 396, (FIG. 16). Inductor 502 and capacitor 504 act as a high pass filter that prevents driving coil voltage pickup in the sensing coil 498 from interfering with the radio frequency current energizing and the desired position sensing action of coil 498. The voltage developed across coil 498 is dependent upon changes in inductance (of the order of from about 7-10 microhenries, for example) in coil 498 that is due to angular movement of the transducer 306 within the transducer assembly.

Diode 510 rectifies the radio frequency voltage across coil 498, and resistor-capacitor network 512 smoothes such rectification into DC voltages proportional to the angular position of transducer 306. These voltages may be on the order of about 0-0.5 volts peak-to-peak, for example, and differential amplifier 514 amplifies such voltage changes to usable levels, such as $-3$ to $+3$ volts DC, for example. Transistor 516 acts as a line driver to operate subsequent load circuits. A relay 518 (which for clarity of disclosure is shown in three places in FIG. 22) disconnects the true position signal to subsequent load circuits and substitutes a fake (theta) frame signal 520 into load circuits whenever head switch 522 is depressed. This is done so that when not in use, mechanical wear on the transducer head assembly is eliminated. The head fits in a small reservoir or "inkwell" holder that activates switch 522 when such head is not in use. At the same time, relay 518 disconnects drive coil current limiting resistors 524 from the head assembly so that the head does not needlessly heat up while resting. Circuitry 526 relays the condition of switch 522 to relay 518. The return wire 528 to switch 522 has a connection to sensing coil 498 in order that, in the event that the head becomes unplugged, relay 518 goes into the idling position and all electronic circuitry is thus protected from the "no signal" condition, which otherwise could be harmful to electronics and cause burns on the phosphor of cathode-ray tube screen 394 if the sector-raster stops and if a bright line were allowed to be scanned.

Figure 23:
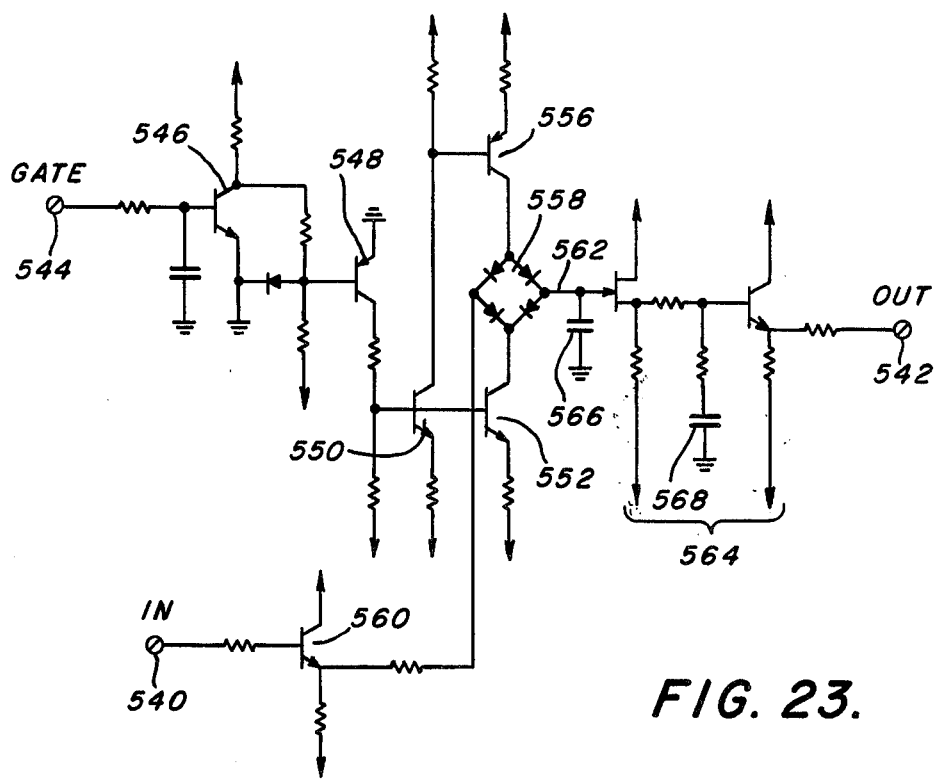
FIG. 23 illustrates a form of circuit usable in the diamond gate sample and hold module of the present invention.

Referring now to FIGS. 16 and 23, there is shown a preferred example of a diamond gate sample and hold circuit 284. The diamond gate sample and hold circuit permits the signals at input 540 to become available at output 542 only when position gate 544 becomes "on," such as at $+5$ volts DC for example. When such gate voltage at position gate 544 turns on transistors 546, 548, this serves to activate current sources 550, 552. Current source 550 turns on upper current source 556, and the current provided by current source 556 may typically be about 5.0 milliamperes, for example, exactly balances and opposes the current of current source 552. These opposed currents do not interfere with the signal transfer process, but rather, such current sources only serve to activate diodes 558 within the diamond gate in order that any input position signal received at 540 relayed by driver transistor 560 becomes available at point 562. Amplifier 564 senses the voltage at point 562 and drives load circuits connected to output 542, while capacitors 566, 568 act as averaging filters in order to cause sequential sampling actions, which, in the example given above, would occur every 370 microseconds, to result in a smoothly varying output voltage that follows the relatively slow mechanical motion of the transducer through its angular path.

Figure 24:
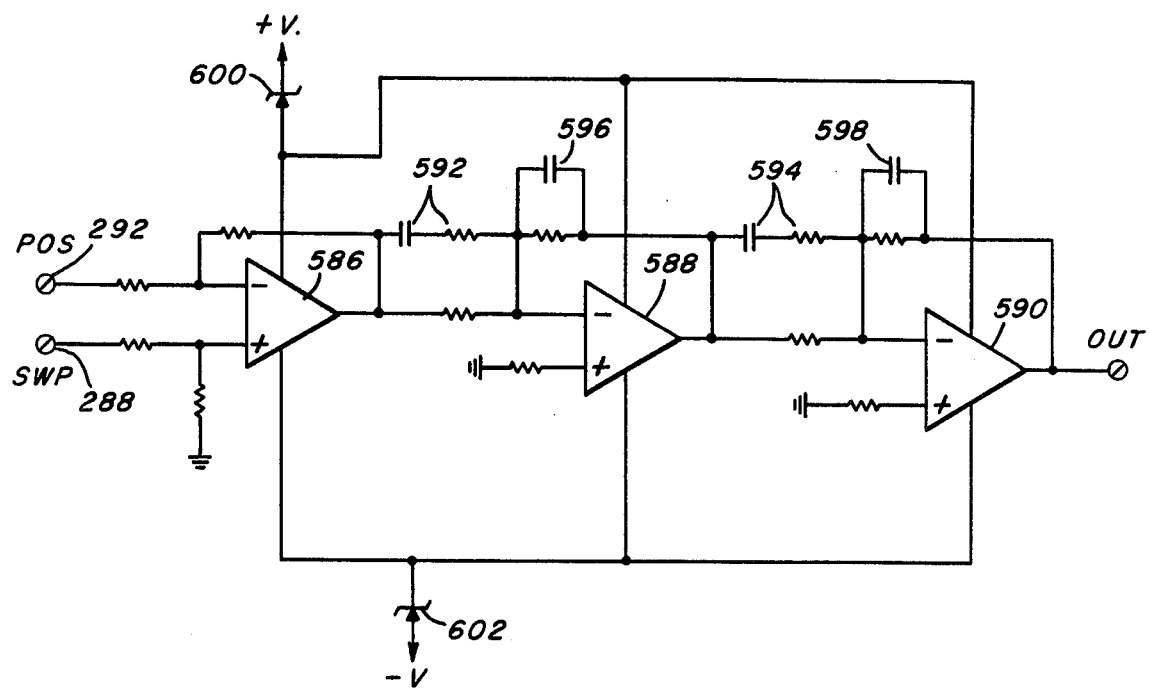
FIG. 24 illustrates a form of servo amplifier and equalizer circuit usable with the present invention.

Referring now to FIGS. 16 and 24, an example of a preferred form of servo amplifier and equalizer circuit 290 will now be considered. The position signals which enter servo amplifier and equalizer 290 through lead 292 is subtracted from the sweep signal which enters servo amplifier and equalizer 290 through input lead 288. This subtraction occurs in operational amplifier 586 and the difference is amplified by additional operational amplifiers 588, 590 which are connected in tandem. Resistor-capacitor networks 592, 594 modify the frequency and phase response of operational amplifiers 588, 590 in order that the completed feedback loop involving the transducer 306 has sufficient stability so that the transducer element 306 will follow the command signal received at input 288 rather than going into uncontrolled mechanical oscillations. Capacitors 596, 598 act as low-pass filters that prevent residual voltage ripples from the diamond gate sample and hold module 284 from being amplified to the same extent as the DC positive sensed signal voltage from the sample and hold module 284. The $+20$ and $-20$ volt DC power is reduced respectively to $+15$ and $-15$ volts, for example, respectively, through Zener diodes 600, 602.

Figure 25:
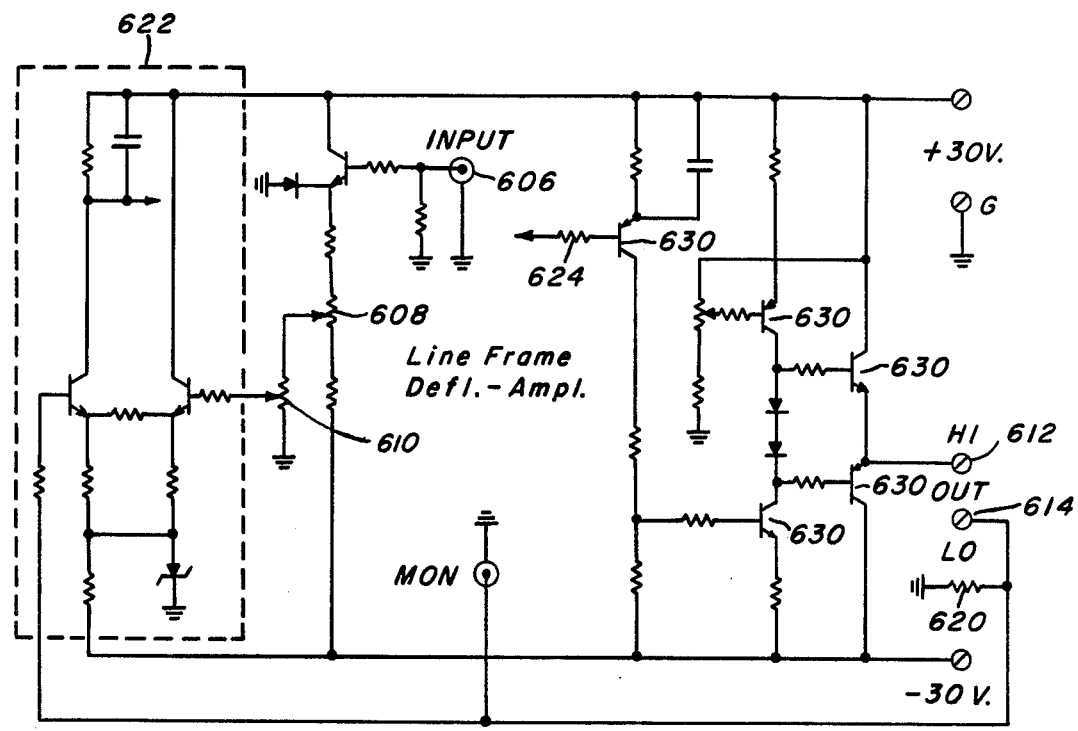
FIG. 25 illustrates a form of amplifier circuit usable in the present invention.

Referring now to FIGS. 16 and 25, there will be illustrated a preferred form of circuit employed for the servo power amplifier 298. This same circuit may be employed for the line power amplifier 400 and the theta power amplifier 402. The input 606 is offset from the centering control 608 before a fraction of such offset signal is tapped at potentiometer 610, and the magnitude of the voltage tapped at potentiometer 610 determines the magnitude of current output at 612. The load, generally consisting of transducer driving coil or one of the deflection yoke coils, is connected between points 612 and 614. Resistor 620 produces a voltage drop of about 4 volts peak-to-peak, for example, for output currents ranging from about 0.2-1.0 amperes, and the voltage drop across resistor 620 is fed back to differential amplifiers 622 which compares the resistor voltage 620 with the tapped control voltage at 610. The difference in voltage is available at point 624 and is fed to the amplifier transistors 630 to produce drive currents at 612 in proportion to the difference signal at point 624. This circuit is a form of standard "complementary-symmetry" power amplifier design, such as those used in high quality cathode-ray tube oscilloscopic-photographic recording systems.

Referring now to FIGS. 16 and 26, a description of a circuit suitable for use in the sectoring programmer 286 will now be considered. This sectoring programmer may be of a conventional triangular waveform type of generator of the Schmidt trigger-integrator variety. The output voltage condition of the Schmidt trigger 640 depends upon the voltage input at 642. When the voltage at 642 is low, such as, for example $+2$ volts and rising towards, for example $+6$ volts, the second transistor 644 conducts current, and the voltage at point 646 is low, for example $+6$ volts. However, when the input voltage at point 642 rises beyond about $+6$ volts, for example, the first transistor 648 conducts, and the second transistor 644 turns off. The voltage at point 646 goes high and remains high (about $+20$ volts, for example) until the input voltage at 642 returns all the way from $+6$ to $+2$ volts. The Schmidt trigger acts as a sort of electronic "toggle switch" in the sense that any input voltage trend must "over-shoot" its mark for the output condition at point 646 to change. When output voltage at 646 is low (about $+8$ volts, for example), transistors 656, 658 become turned on, and the upper current source 660 becomes turned off. During this condition, the lower current source 662 takes over, and capacitor 666 discharges. Transistors 668, 670 amplify the available current from capacitor 666 without distorting the voltage waveform seen across capacitor 666. The output signal at point 672 can only continue so far until the upper current source 660 becomes activated (or shut off) and, thus, the output voltage at point 672 consists of a triangular-shaped waveform with straight ramps along the sloping portions of the waveform, such as that shown adjacent in the insert generally above point 672 in the plot of voltage versus time. Potentiometer 674 determines how much of the triangular waveform is to be used to control the angular position of transducer 306. The degree of transducer deflection is proportional to the percentage voltage tapping set by potentiometer 674. (The angular deflection in degrees is equal to the percentage of voltage tap times the voltage at point 672.) A voltage tap setting from potentiometer 676 sets the constant current of about 1.5–6 milliamps, for example, available from both constant current sources 662, 678. However, while the current source 662 discharges capacitors 666 directly, current source 662 indirectly affects the charging action through current source 660. Whenever transistor 658 conducts, current source 660 becomes turned off. Resistor 686 is set lower than resistor 688 in order that the magnitude of current (about 3–12 milliamps) available from the upper current source 660 is twice the current available from the lower current source 662. However, the voltage available from potentiometer 676 controls both current sources 660, 662 in a tracking manner. These currents are set high, the triangular waveform repeats at about 13 Hz rate (corresponding to 26 frames per second) in the image, and when these currents are set low, the triangular waveform repeats at about 5 Hz (corresponding to 10 frames per second) in the image.

Referring now to FIGS. 16 and 27, a circuit for a preferred form of chirp programmer 314 suitable for use with the present invention will now be considered. The chirp programmer 314 receives the active gate signal from master timer module 280 over leads 312, 316 at input 700. The chirp programmer provides two types of output signals. The first type is a chirp duration gate pulse which is available at output 702 and may last about 4.5 microseconds, for example. This signal is delivered to chirp transmitter 324 over lead 318. The other type of output is the chirp slew signal which is available at output 704 and is delivered to chirp transmitter 324 over lead 320. Typical waveforms are illustrated in FIGS. 27(a), 27(b) and 27(c). The active gate signal is illustrated in FIG. 27(a); it has a generally rectangular wave configuration with a maximum amplitude of five volts and a duration of about 136 to 266 microseconds, for example. The chirp gate signal is shown in FIG. 27(b) and has a duration of about 4.5 microseconds and a maximum amplitude of 5 volts, for example. The chirp slew signal is illustrated in FIG. 27(c). It has essentially the same time duration as the chirp gate signal, but does not have the rectangular shape. The time that the chirp gate pulse, which is available at output 702, is on determines how long the chirp transmission occurs. The shape of the sloping portion of the chirp slew signal available at output 704 determines how the radio frequency varies within the chirp. The instantaneous frequency within the chirp is directly proportional to the height of the chirp slew wave. A good approximation is to relate 1.0 volt of chirp slew command at point 704 for every 1.0 MHz of frequency increase in the radio frequency transmission of the chirp.

The active gate signal received at input 700 triggers the one-shot multivibrator 706 that produces the 4.5 microsecond pulse. A suitable form of multivibrator for this purpose is disclosed in U.S. Pat. No. 3,964,296, and others are well known to those skilled in the art. The output of multivibrator 706 is available at point 702 and also triggers the slew circuitry at point 708. Between chirps, transistors 710, 712 are normally conducting, and thus they turn off current sources 714, 716, during this quiescent. No charging current is supplied to capacitor 718 through transistor 714 or 716 and only resistor 720 determines the average resting voltage on capacitor 718. Potentiometer 722 sets the resting voltage level of capacitor 718 between chirps. This resting voltage level determines the initial height of the sloped slew waveform which is available at output 704. When the chirp gate output becomes active at output 702, point 708 activates transistors 724, 726 to enable current sources 714, 716 to oppose each other in the quest to charge capacitor 718. Depending upon the position of the wiper of the symmetry potentiometer 728, either the upper current source 714 or lower current source 716 will dominate, and the direction of the slope in chirp slew waveform at output 704 will either show an upward or a downward trend. Diodes 730, 732 prevent the slew output from going negative under any condition, and transistor 734 is simply a line-driver to drive the loading circuit external to the module.

The chirp transmitter 324 works in a manner similar or identical to the way in which sectoring programmer 286 works, however, the chirp transmitter 324 works in a very high frequency range, such as about 1–4 MHz, for example.

Figure 28:
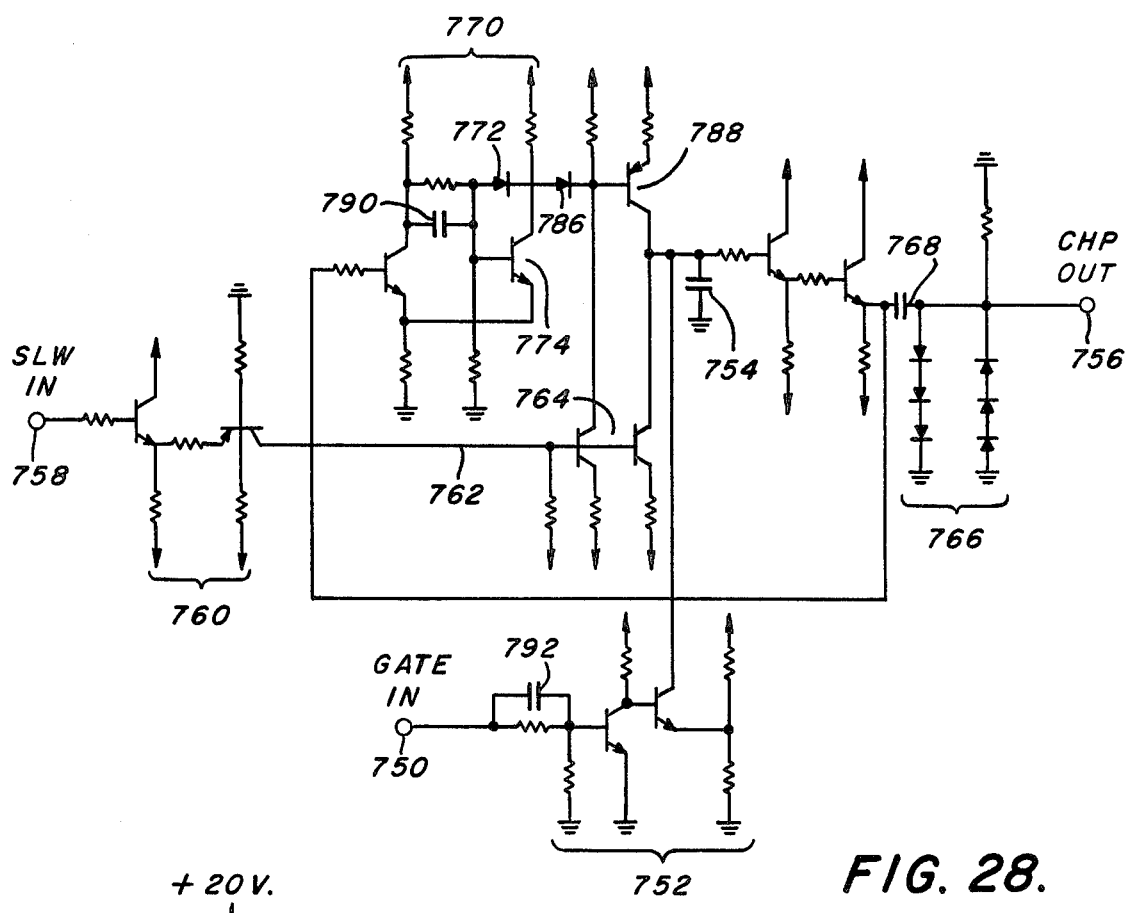
FIG. 28 illlustrates a form of chirp transmitter circuit employable with the present invention.

Referring now to FIGS. 16 and 28, a description of a preferred form of circuit for the chirp transmitter 324 will now be considered. When chirp gate input 750 is on, transistor circuit 752 allows capacitor 754 to be unlocked from the grounded position, and the output waveform becomes available at output 756. The ramp function control slew signal at slew input 758 is amplified by transistors 760 and the output at 762 programs current source 764 in order that the charging/discharging rates affecting capacitor 754 are dependent upon the slew command signal received at 758. The array of diodes designated 766 and capacitor 768 work together to combine transient overshoots in the output waveform within about 4.0 volts peak-to-peak. The Schmidt trigger 770 contains Schottky clamping diode 772 in order to allow the trigger 770 to work at very high frequencies by reducing the storage time in transistor 774. Diode 786 also speeds up the operation of Schmidt trigger 770 by disconnecting the base capacitance of transistor 788 from loading transistor 774 during the turn-on phase of operation of transistor 774. Capacitor 790 allows the Schmidt trigger 770 to operate faster by compensating for the base capacitance effect of transistor 774. Likewise, capacitor 792 compensates for delay time (about 0.2 microseconds, for example) in the waveform enabling circuitry 752.

Figure 29:
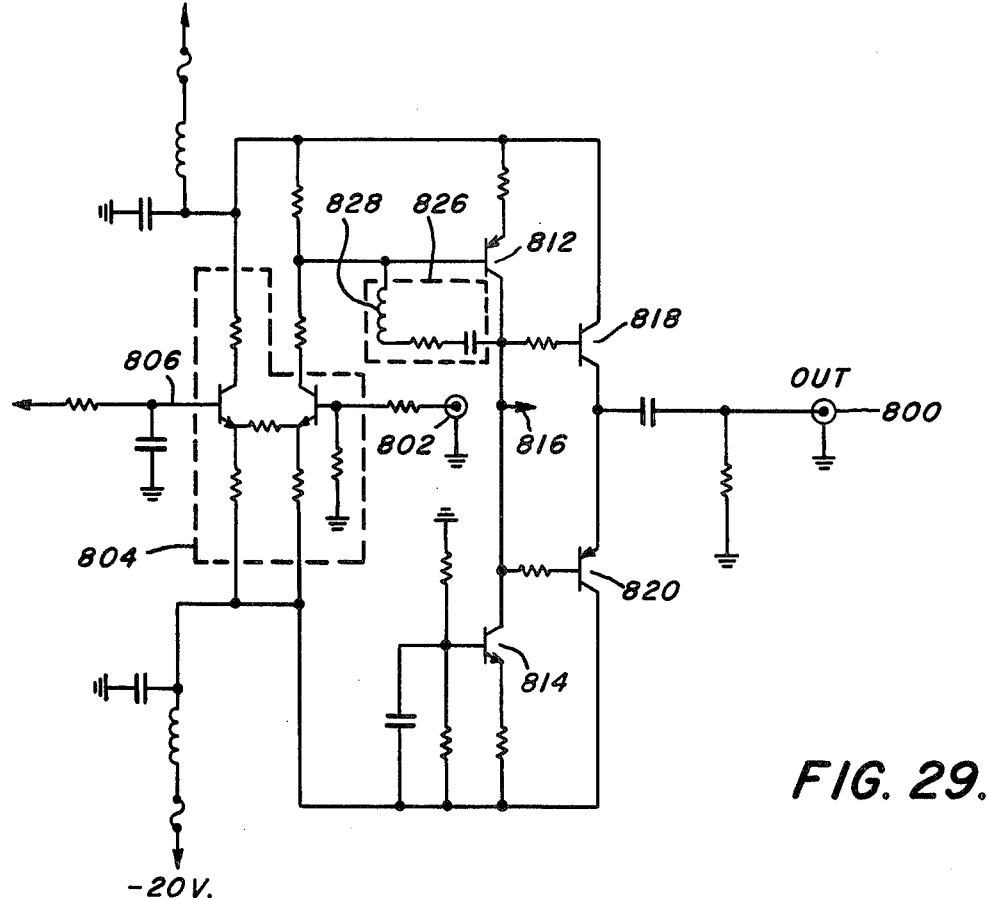
FIG. 29 illustrates a form of circuit for a chirp power amplifier usable with the present invention.

Referring now to FIGS. 16 and 29, a preferred form of circuit for chirp power amplifier 330 will now be considered. The chirp power amplifier of FIG. 29 works on the principle of compound feedback. This is done in order to maximize DC stability of the amplifier while maintaining frequency response and controlled amplification independent of load conditions. The load applied at point 800 is heavily capacitive, ranging, for example, from about 0.002 to 0.004 microfarads and is caused by the transducer 306 and the connecting cable between point 800 and the transducer 306. Drive currents on the order of several amperes can occur at radio frequencies ranging from about 1 to 4 MHz, for example.

The signal from the chirp transmitter 324 is applied to point 802 via lead 326 (FIG. 16). Point 802 feeds one side of differential amplifier 804. The other signal at point 806 is a low-pass filtered version of the average DC voltage split between the driver transistors 812, 814. The average voltage difference between points 802 and 806 is compared in differential amplifier 804, and this comparison through feedback sets the DC voltage level at point 816 at 0.0 volts DC. The feedback through point 806 is not related to the ability to amplify the chirp signal. This feedback only "centers" the bias condition of the entire amplifier 804, and thus permits maximum possible output voltage (about 36 volts peak-to-peak, for example) to be obtained for all input frequencies. The output transistors 818, 820 follow the voltage seen at point 816, except for a small amount (about 1.2 volts, for example) of cross-over distortion which is designed into the power amplifier in order that this amplifier 804 will not pass small signals, such as residual parasitics through power supply leads when the power amplifier is supposed to be turned off. The expression "cross-over distortion" refers to the portion of the plot of voltage versus time wherein a portion of the wave, as it crosses the zero voltage level is not amplified, i.e. goes through a "dead zone" in the amplifier. Network 826 comprises the second feedback network that sets a uniform gain of about 10 to 1, for example, for the amplifier 804 over the frequency range from about 0.5 to 6 MHz, for example. It is noted that the inductor 828 in this network 826 compensates for loss in high frequency response, which is most severe in transistors 818, 820. The employment of network 826 allows the gain of the power amplifier 804 to be independent of the changes in transducer to transducer connected as a load. Also, the transducer undergoes a piezoelectric resonance variation at impedance near 2.25 MHz and network 826 also compensates for this effect. Among the suitable transistors usable for transistors 812, 814, 818, and 820 are those sold under the trade designation Motorola Type MPSU56 and MPSU03 which are special "uniwatt" transistors, that represent a compromise between power-handling ability and frequency response.

Figure 30:
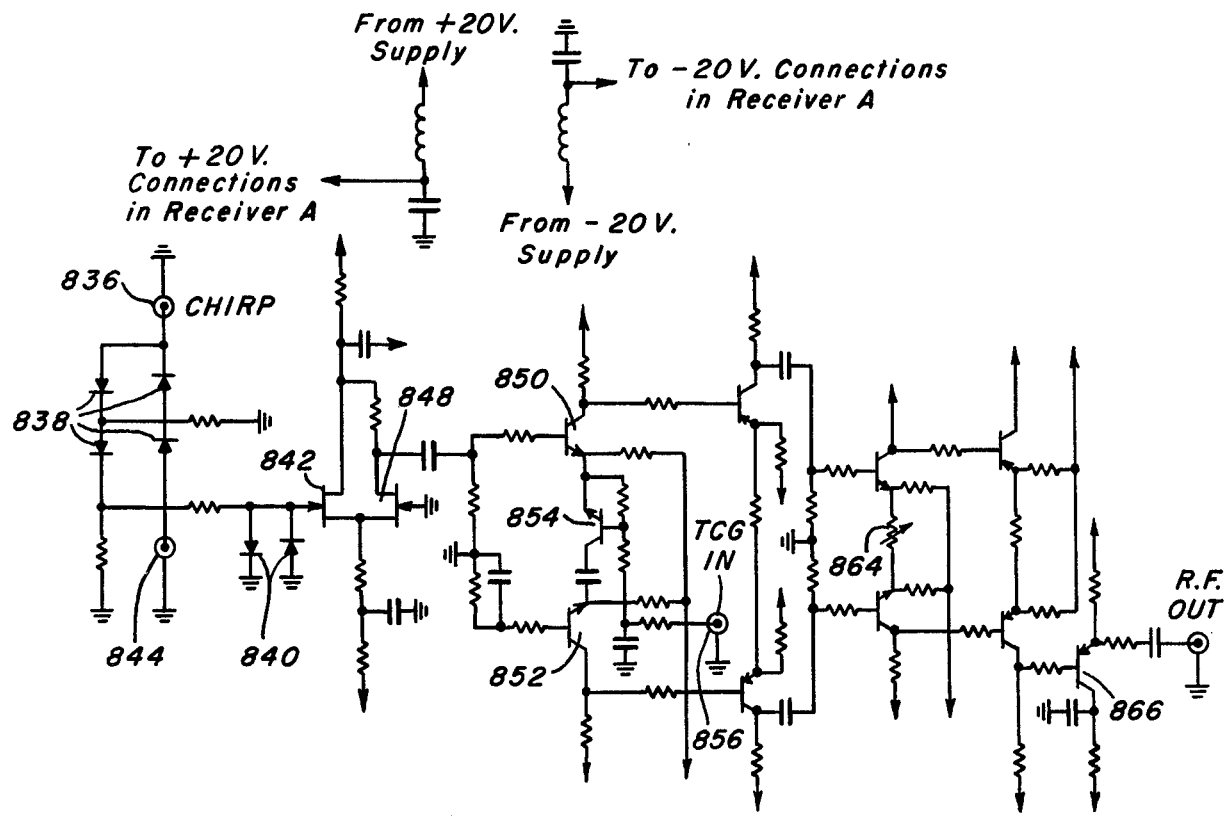
FIG. 30 illustrates a form of circuit for a receiver usable in the present invention.

Referring to FIGS. 16 and 30, an example of a circuit employable receiver 340 will now be considered. This receiver may be of a conventional variety. The chirp signal from chirp power amplifier 330 is applied to receiver 340 by means of lead 342 and is received at input 836. Diodes 838 isolate the chirp power amplifier from the feeble transducer reflection signals (at 844) from the test specimen. Diodes 840 protect the field-effect transistor 842 from the high voltage chirp signal. The transducer cable is connected at point 844. This is accomplished by means of lead 846 which connects transducer 306 with the receiver 340 (See FIG. 16). Field-effect transistors 842, 848 act together as a low-noise differential input amplifier. The output of this amplifier feeds transistors 850, 852 which are the beginning of a four-stage differential amplifier. The transistor sprung at 854 acts as a variable conductance device. When the conductivity of transistor 854 is high, the gain of the entire receiver 340 is also high. The conductivity of transistor 854 is controlled by an input signal from TCG module 344 which is delivered to receiver 340 by means of lead 858 (FIG. 16) with delivery being at point 856. The master gain control of receiver 340 is a twelve-position selection of resistors shown generally at point 864. Transistor 866 is a line driver amplifier that operates the input of the pulse compression filter 346 (FIG. 16). It will be noted that a large number of the circuits within receiver 340 are differential because the differential design approach minimizes the number of coupling capacitors between adjacent amplifier stages. This minimization is desirable as a receiver so designed recovers more quickly from the large "blast" of power from the chirp transmitter 324. Another advantage is that it is possible to design a very sensitive switch receiver without the use of transformers which may be susceptible to magnetic interferences by using a larger number of transistors. This approach is also more economical.

Figure 31:
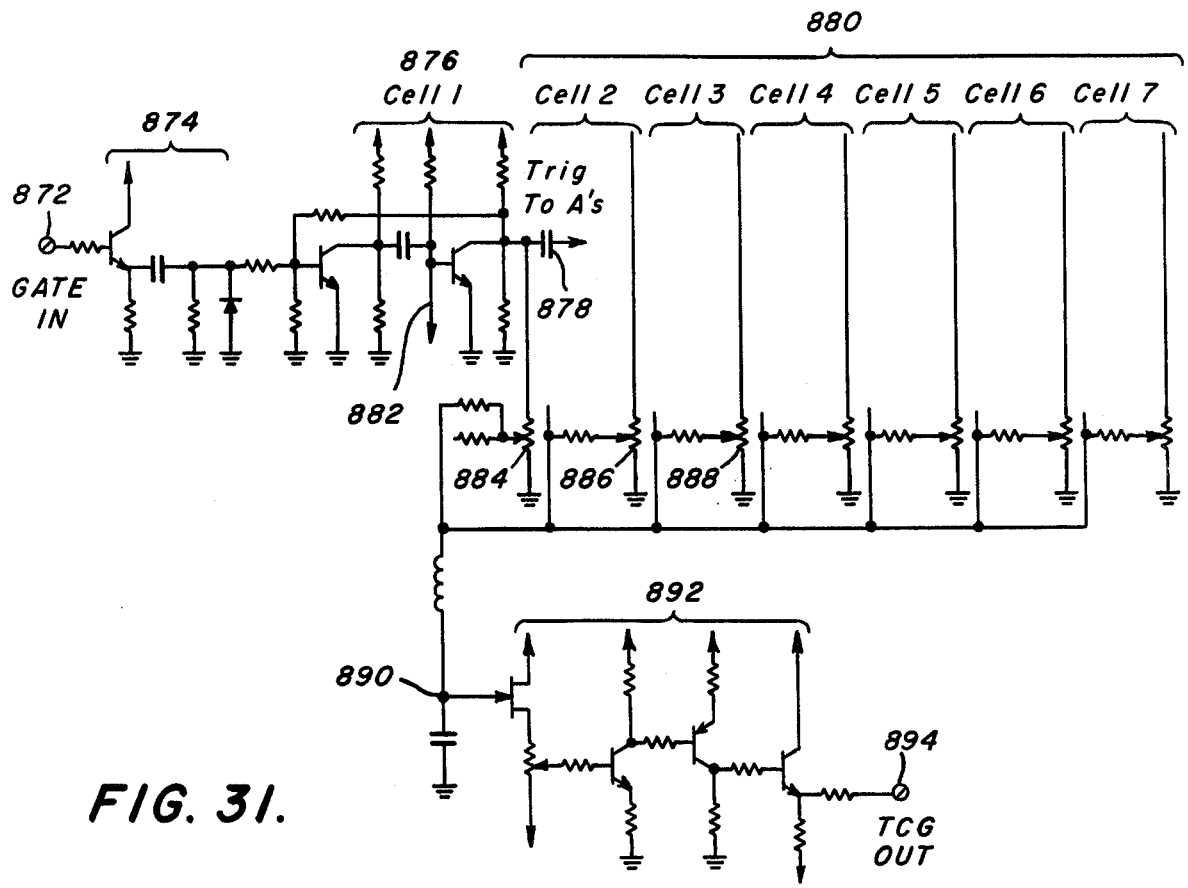
FIG. 31 illustrates a form of time-controlled gain module circuit employable with the present invention.
Figure 32:
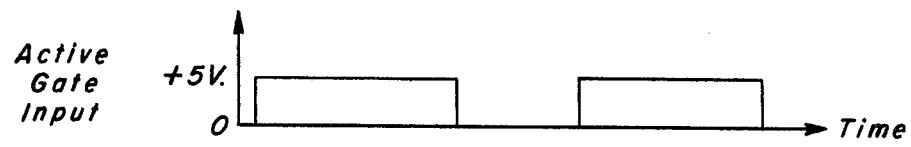
FIGS. 32 through 35 illustrate voltage versus time plots of various signals at various stages within the time-controlled gain module.
Figure 33:
Figure 34:
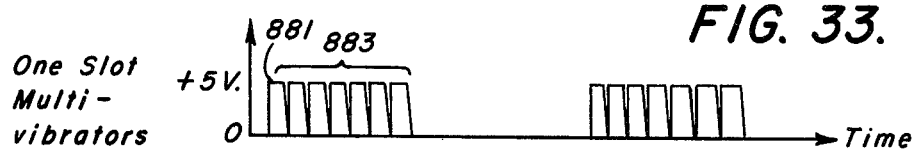
Figure 35:
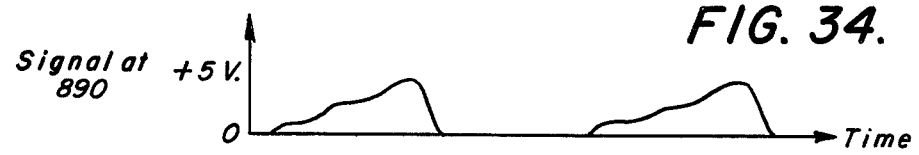

Referring now to FIGS. 16 and 31, a form of circuit suitable for use in TCG module 344 will now be considered. The active gate signal emitted by the master timer module 280 is delivered to the TCG module 344 by way of leads 312, 406, 868, and is applied at input 872 of the TCG (time-controlled gain) module 344. Transistor circuit 874 differentiates the gate pulse so that the leading edge of the gate pulse initiates a 20 microsecond, for example, "on" time of multivibrator 876. (As all stages of the multivibrator may be essentially identical, cell 1 has been identified by the reference number 876, and cells 2-7 have been shown in general fashion and identified collectively by the number 880.) Capacitor 878 causes the second one-shot multivibrator in the series of seven to become "on" during the falling edge of the pulse from the first multivibrator 876. In this fashion, each of the cells of the multivibrators 876, 880 are sequentially activated to produce 20 microsecond pulses, for example, in the fashion shown in FIGS. 32–35. FIG. 32 shows the rectangular wave active gate input signal which has, in the form shown, a maximum voltage of +5 volts. FIG. 33 shows the differential leading edge and clamped trailing edge (non-existent) of the active gate pulse. Such a differential pulse initiates the first one-shot 20 microsecond pulse 881 of FIG. 34. The cells of 880 (FIG. 31) produces the following pulses 883. For every "on" condition of cells 876, 880 (FIG. 31), potentiometers 884, 886, 888, etc. tap from 0 to 5 volts, resulting in a "boxy" staircase waveform resembling the physical settings of adjacent potentiometers 884, etc. The filtered staircase function, shown in FIG. 35, represents the smoothly programmable TCG waveform function.

Within each multivibrator cell the trigger capacitor 878 connects to point 882 as indicated in multivibrator 876. The series of potentiometers 884, 886, 888, etc. provide a single potentiometer for each multivibrator or multivibrator cell as designated above. The potentiometers sample the height of each pulse from each multivibrator 876, 880. As in this example, there are seven such potentiometers, sampling each of seven pulses, a staircase waveform is obtained, and such waveform is smoothed at point 890 to correspond to a gradually changing signal at 890. Such a signal is shown in FIG. 35, with the staircase signal being shown in FIG. 34. The waveform at point 890 is amplified by amplifier 892, and the final output waveform from output 894 becomes the time-controlled gain control signal that is applied to receiver 340 through lead 858 (FIG. 16). It should be noted that this waveform is generally monotonically increasing to correspond to increasing receiver gain requirements as against time, and that time is proportional to depth within the specimen. Each of the seven potentiometers 876, 880 illustrated are of the linear slide-pot variety, and are mounted on a front panel convenient to the ultrasonographer so that adjustments of increasing gains can be made to suit the particular test specimen being examined or treated. Different test specimens may require different TCG settings because some test specimens absorb more sound than others. For example, in human patients, such variables as age difference, degree of hydration and variations in muscle and fat layers could alter the sound absorption characteristics. The receiver 340 sensitivity increases at the rate of about 5 dB per +1.0 volt increase in TCG control signal, and a TCG range of about 25 dB (0 to +5 volts DC) is attainable.

Figure 36:
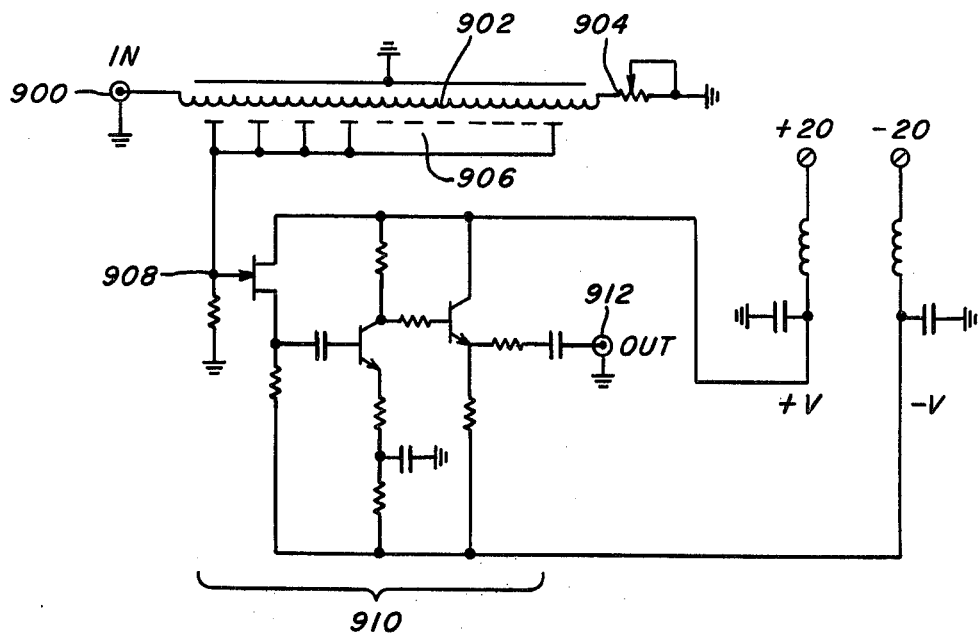
FIG. 36 illustrates a form of compression filter circuit usable in the present invention.
Figure 37:
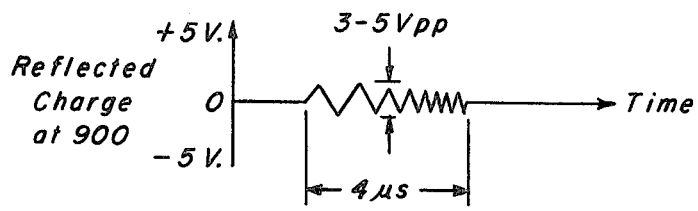
FIGS. 37 and 38 are voltage versus time plots illustrating signal changes within the compression filter circuit.
Figure 38:
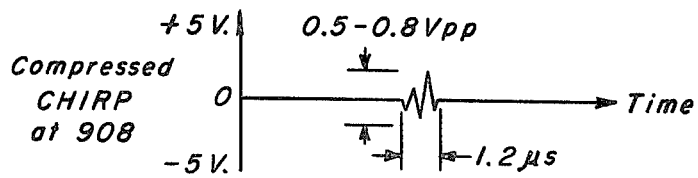

Referring now to FIGS. 16 and 36, a form of circuit suitable for use in compression filter 346 will now be considered. The compression filter circuit illustrated in FIG. 36 is a multitapped weiner filter designed around a four microsecond, for example, distributed delay line. The signal from receiver 340 is applied at point 900 and passes down the coil of 1500 turns of #30 Type ML magnet wire wound on a one inch diameter Lucite tube 24 inches long, for example. The tube was initially provided with a half circle wrap of aluminum downspout repair tape, and this tape was connected to the electrical ground of the filter casing. The combination of coil and ground shown schematically and identified by the reference number 902 form a four microsecond delay line that has a surge impedance of 560 ohms, for example. This line is critically terminated for zero reflection coefficient by trimpot 904. Usually from about eight to 10 capacitive taps 906 are provided by two wraps of #22 solid tinned copper hookup wire, and each tap is positioned so that the casing for the entire tap configuration bears a resemblance to the shape of the transmitted chirp signal. The capacitive tap samples the fully developed chirp from the test specimen when the entire chirp reflection occupies the entire line and provides the greatest pulse output waveform during the time that most of the reflected chirp happens to be in the line. The signal available at point 908 represents a very short radio frequency signal of the frequency corresponding to the center (average) chirp frequency, and the duration of the signal at point 908 depends upon the setting of the sampling points 906. In general, it is possible to compress the length of the original chirp from four microseconds, for example, to about 1 to 1.5 microseconds. As is shown in FIGS. 37 and 38, the compressed chirp at point 908 suffers from about 10 to 1 attenuation in amplitude because many capacitances have a shunting effect on one another during the sampling process. FIG. 37 illustrates the reflected chirp at 900, while FIG. 38 represents the compressed chirp at 908. Amplifier 910 raises the amplitude to approximate the original signal amplitude of about 5 to 8 volts peak-to-peak, and the output at output point 912 drives receiver 350 through lead 352 (see FIG. 16). It should be noted that impulse and Johnson (thermal noise) noise from receiver 340 is to a significant (about 15) degree dB attenuated by the compression filter 346 as the output at 912 (and the remaining system response) is now biased to favor only those signals coming in at 900 that satisfy the particular pulse compression code which closely approximates the original chirp being transmitted, which is generally chosen to be a simple tone-burst of rising frequencies. The compression code is determined by the slew output 704 of the chirp programmer 314.

Figure 39:
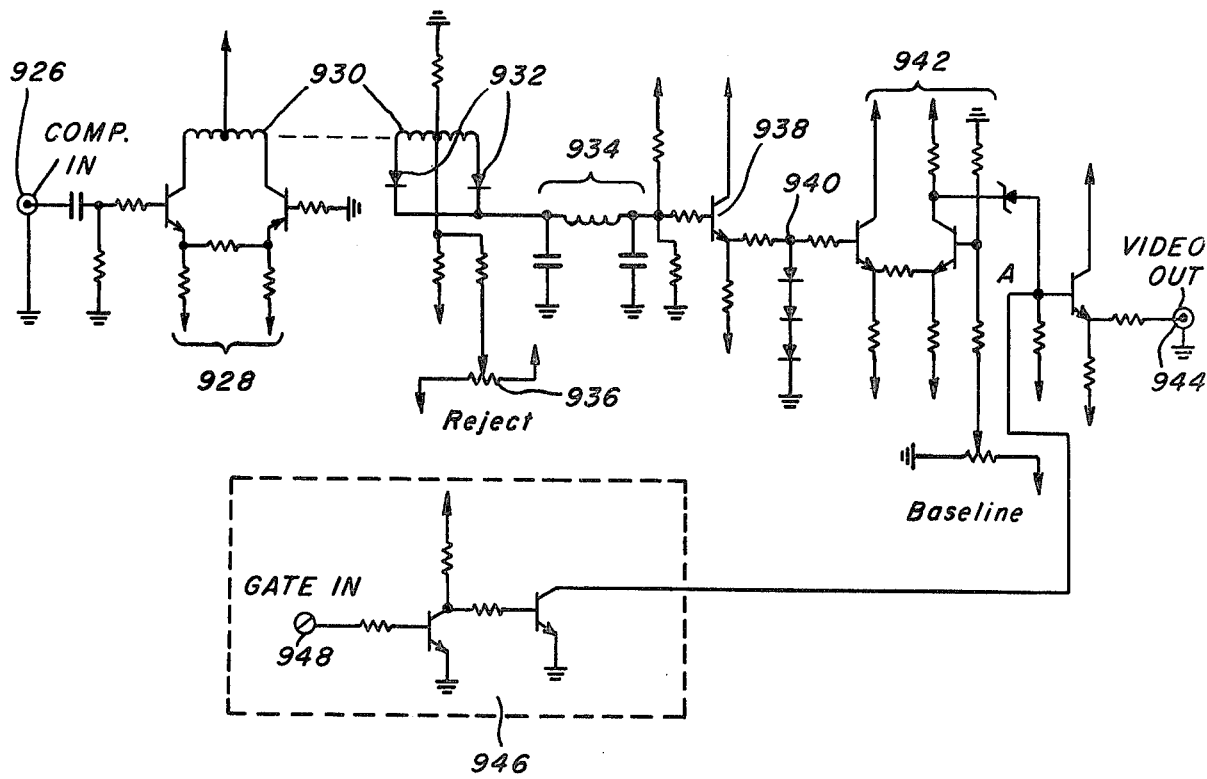
FIG. 39 illustrates a circuit for a form of receiver suitable for use in the present invention.

Referring now to FIGS. 16 and 39, a form of receiver 350 suitable for use in the present invention will now be considered. The output from compression filter 346 is introduced into receiver 350 through lead 352 at input point 926. Differential amplifier 928 drives the primary of transformer 930. The secondary of transformer 930 operates the full-wave rectifier diodes 932 and the envelope information is separated from the radio frequency signal by the pi-network low-pass filter 934. Reject potentiometer 936 applies a controlled amount of reverse voltage bias to rectifier diodes 932 in order that low amplitude (0.1 to 0.4 volts peak-to-peak, for example) radio frequency voltages do not pass through the rectification stage. Emitter follower 938 provides the amplified current necessary to drive logarithmic diode converter 940. The voltage at logarithmic diode converter 940 represents a compressed, dynamic range rendition of the rectified signal from filter 934. In order to restore the logarithmic conversion to the desired (0 to +5 volts DC) signal output, differential amplifier 942 is employed. The voltage at 944 is a video signal that represents the raw picture information from the internal anatomy of the patient, in the case of a human test specimen. In order to prevent receiver 350 from responding at a time other than the picture display time (for the appropriate magnification) the active gate signal is applied to gate circuitry 946 that enables the output of amplifier 942 to be present only during the active gate "on" time (in the example given above, this would be 136, 200 or 266 microseconds). The gate signal is delivered to receiver 350 by means of leads 312, 406, 868 and 948. It will be appreciated that receiver 350 may be of a conventional nature.

Figure 40:
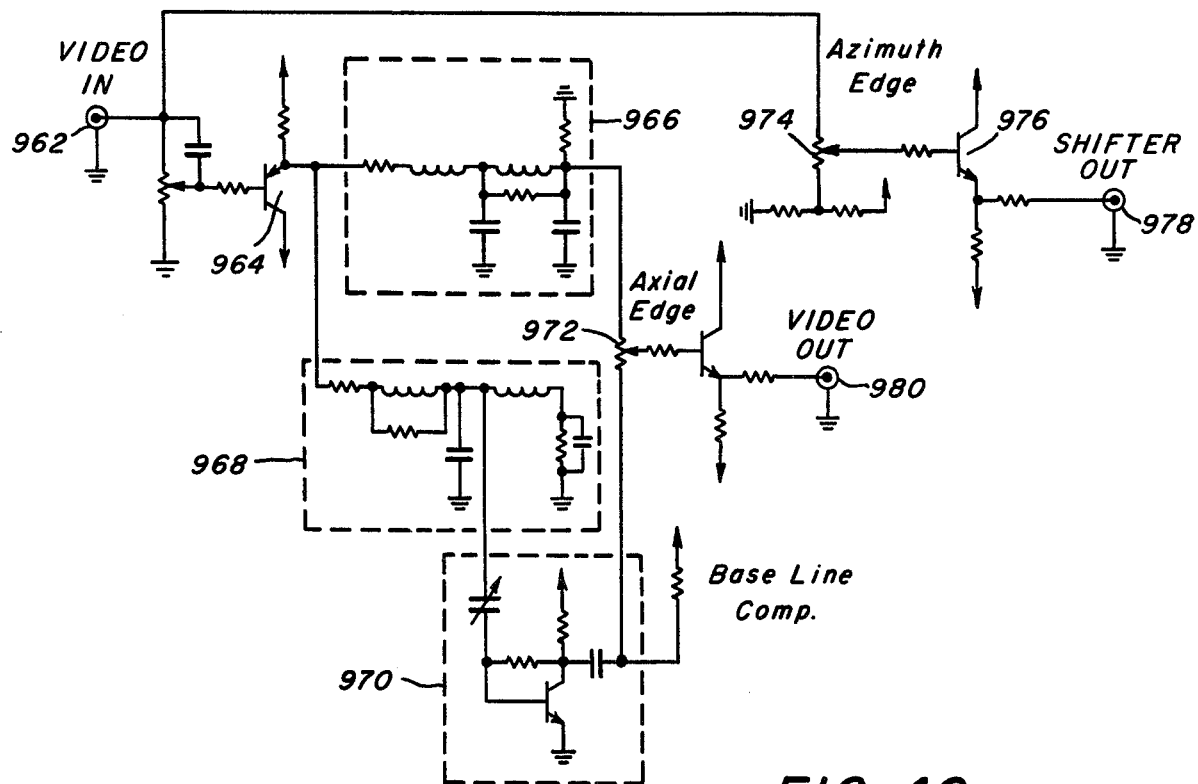
FIG. 40 illustrates a form of circuit for a contrastor module usable with the present invention.

Referring now to FIGS. 16 and 40, a description of a form of circuit adapted for use in the contrastor module 360 will now be considered. The video output from receiver 350 is received at point 962 in contrastor module 360 through lead 362. The transistor 964 increases the available current to run filters 966, 968. Filter 968 is a low-pass filter that feeds differentiator 970. The objective is to restrict the bandpass to about 1.0 MHz, for example, before differentiating the leading and falling edges in the video voltage. Filter 966 is a simple time-delay filter that aligns, in time, the original video voltage with the differentiated signal at potentiometer 972. Depending on how low the wiper position is on potentiometer 972, more of the differentiated video is added to the original video, and the downward wiper positions correspond to increased axial edge enhancement. Examples of waveforms as they would appear entering point 962, filter 966, differentiator 970 and potentiometer 972 are shown respectively in FIGS. 41 to 44 and will be described below. The objective is to increase the steepness of the slope of the leading and trailing edges of the video signal at potentiometer 972, thus increasing the sharpness of the display image in the vertical direction.

Part of the original video signal applied at point or input 962 is transferred and tapped by potentiometer 974. This tapped percentage of the video signal is amplified by transistor 976 and made available at output 978 to power the "shifter" azimuth edge enhancement circuit. The output at 980 is transmitted to video module 382 over line 384 (see FIG. 16).

Figure 41:
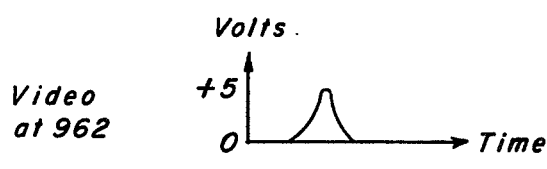
FIGS. 41 through 44 are voltage versus time plots of the changes in the signals within the circuit of FIG. 40.
Figure 42:
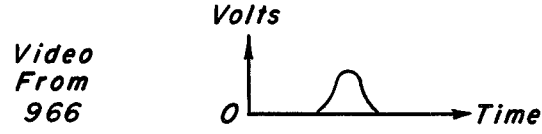
Figure 43:
Figure 44:
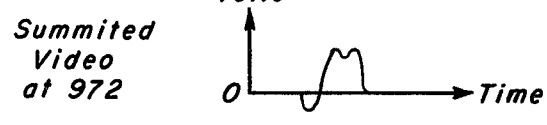

Shown in FIG. 41 is the signal representing voltage versus time of the output from receiver 350 as introduced into contrastor module 360 at point 962. FIG. 42 illustrates the signal as it exits time-delay filter 966. FIG. 43 represents the signal at output point 972 from differentiator stage 970. FIG. 44 represents the composite (summed) time-delayed video (966) and differentiated video 972. The relative emphasis of leading and trailing edges over normal (delayed) video is governed by the setting of potentiometer 972. The time-delay circuits 966 and 968 are used to phase the differentiation process so that a nearby symmetric edge enhancement occurs both in front of and behind each video pulse.

Figure 45:
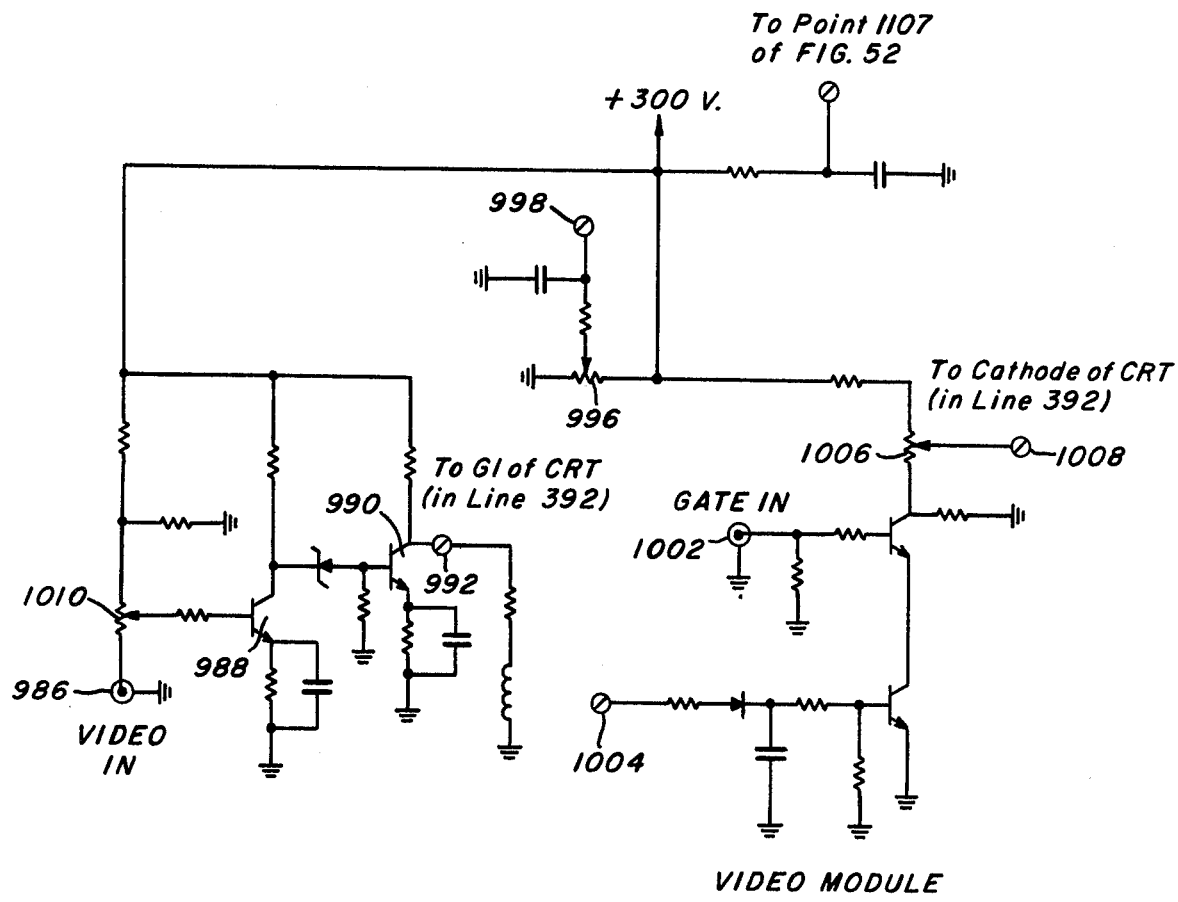
FIG. 45 illustrates a form of circuit usable in the video module of the present invention.

Referring to FIGS. 16 and 45, a circuit suitable for use in the video module 382 will now be considered. The video output from contrastor module 360 is received at point 986 by way of lead 384. Transistors 988, 990 amplify the 5 volt peak-to-peak video voltage signals to about 40 to 50 volts peak-to-peak, and this amplified voltage is applied through point 992 to the control grid GI of the cathode-ray tube assembly 374 through lead 392. A suitable cathode-ray tube assembly 374 for use in this invention is a 5AHP2A magnetic deflection, electrostatic focus cathode-ray tube. A portion of the +300 volts DC that run the video module 382 is tapped by potentiometer 996 and the tapped portion of the voltage is applied through point 998 to the focus electrode of the cathode-ray tube assembly 374 through lead 392 (FIG. 16). The active gate pulse is applied to point 1002 by way of leads 312, 406, 868, 948, 1003 to allow the brightness circuitry to operate. Otherwise, the beam current may be turned off, and the cathode-ray tube screen 394 remain dark.

Referring still to FIG. 45, a connection at point 1004 is provided to protect the cathode-ray tube phosphorus from burns. Although a display picture consists of both line scanning and theta scan (to form the complete sector), at least one form of the scan must be present in order that the beam of the cathode-ray tube does not stand still at one point on the face of the cathode-ray tube screen 394, which action could cause a concentration of energy at a single dot location. Whenever the vertical line portion of the sector scan is present, the signal from the line deflection yoke coil is applied to the 1004 point terminal, and the pressure of voltage at point 1004 permits the brightness circuitry to work properly. As a result, it will be appreciated that the brightness circuitry is keyed by two types of control signals: (a) the active gate pulse and (b) the presence of voltage at point 1004. When both voltages are present, brightness potentiometer 1006 reduces the voltage at point 1008 in order that the cathode-ray tube voltage at 1008 is not more than 40 volts above the average voltage at the control grid point 992. Of course, the operator can modify the exact offset of voltage at 1008 in order to set the average cathode-ray tube screen brightness from a front panel control. Potentiometer 1010 (which may conveniently be a screwdriver operated trimpot) determines a percentage of the video voltage actually being amplified for application to point 992, and thus potentiometer 1010 sets the master contrast for the entire imaging system.

Figure 46:
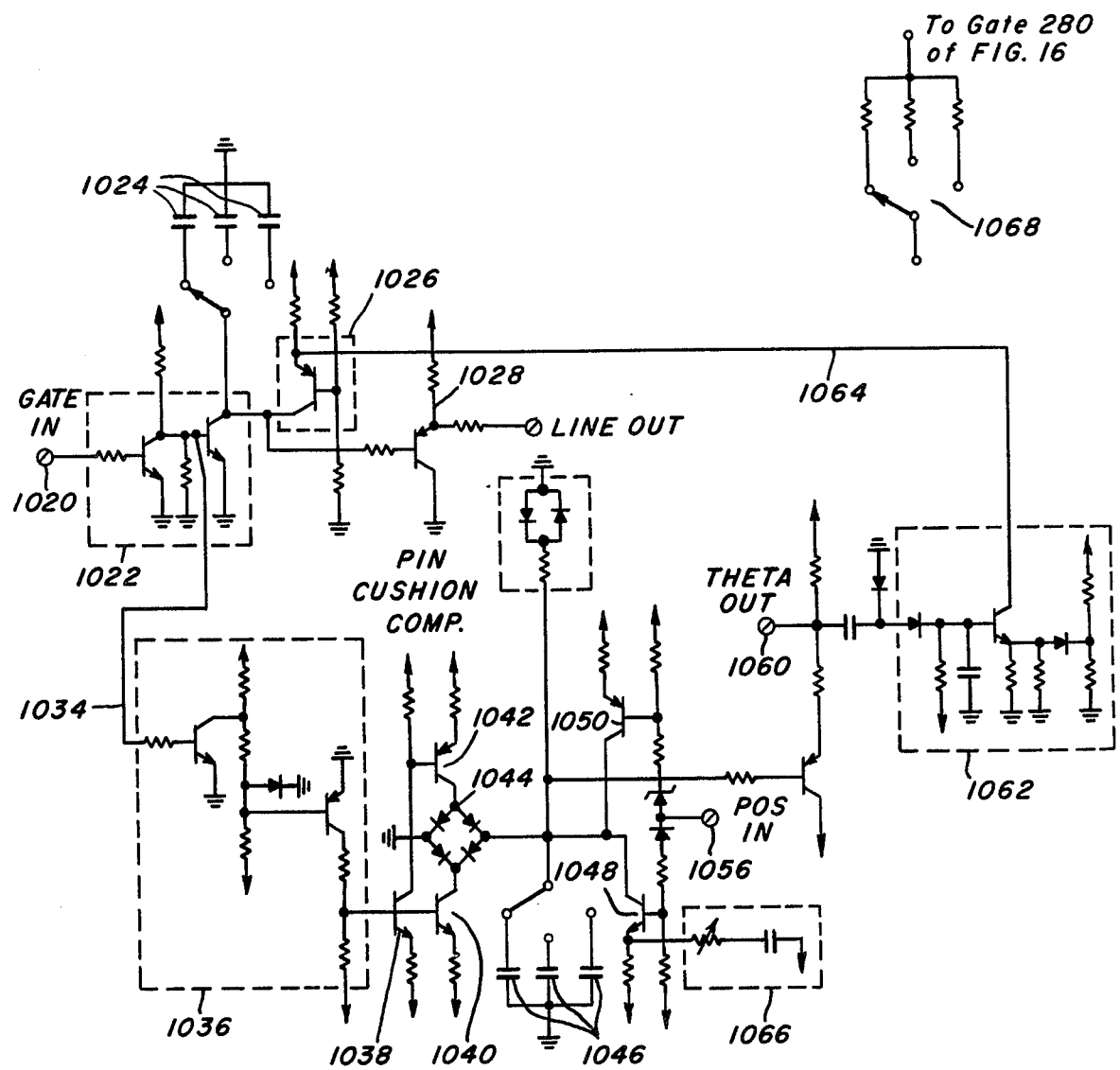
FIG. 46 illustrates a form of circuit suitable for use in the sector display sweep generator of the present invention.
Figure 47:
FIGS. 47 and 48 show changes in the signal which occur in the sector display sweep generator.
Figure 48:
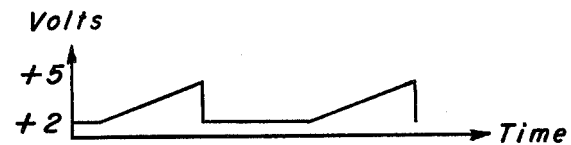

Referring now to FIGS. 16 and 46, there is shown a circuit for a form of sector display sweep generator 398 suitable for use in the present invention. The active gate pulse is applied to input point 1020 by way of leads 312, 406, 868, 408 in order to activate the entire generator. Two types of output signals are provided by the sector display sweep generator 398. The first type of signal is a sawtooth ramp signal voltage, which, may, for example, have a voltage of about +2 to +6 volts. This sawtooth ramp signal voltage represents the downward going line deflection signal. The second type of signal, which may, for example, be within the same voltage range as the first signal is a reversible sawtooth ramp signal voltage that represents the theta scan portion of the deflection signal. The combination of both output signals, when amplified and applied to the deflection yoke of the cathode-ray tube assembly 374, generates the sector display raster format on the cathode-ray tube screen 394. The active gate signal which is provided in input 1020 causes transistor clamp circuit 1022 to turn off, thereby enabling one of the three capacitors 1024 to charge along a positive going linear ramp. Current source 1026 provides the constant charging current, and amplifier 1028 provides the necessary current drive capabilities to power external load circuits. A plot of voltage versus time showing the active gate signal as applied to input 1020 is shown in FIG. 47, and the output from amplifier 1028 is shown in FIG. 48. The active gate signal is relayed through lead 1034 to operate control circuitry 1036. This circuit 1036 activates current sources 1038, 1040 and 1042 only during the in-between times when the active gate pulse is "off." During the "off" times, diamond gate 1044 causes one of the three capacitors 1046 to discharge back to zero volts DC. However, during the "on" time of the active gate pulse received at point 1020, one of the three capacitors 1046 is free to charge along linear ramps through the competitive current sources 1048, 1050.

The angular position signal from the diamond gate sample and hold module 284 (FIG. 16) is applied to point 1056 (FIG. 46) via lead 1058 (FIG. 16), and, depending upon the polarity and magnitude of signal at 1056, either current source 1048 or current source 1050 will dominate in the sense and severity of either domination determines the magnitude and direction of the ramp charging waveform building up during the gate active time on one of the three capacitors 1046.

The theta output waveform which appears at output 1060 thus follows the position signals in order that the waveform at 1060 correspond directly to the angular position of transducer 306. Circuit 1062 provides a control signal on lead 1064 which reduces the current available from current source 1026. This serves to make the displayed sector vertically shortened and approximates the radius at the bottom to give the sector image raster the curved outer edge of a "pie-slice" type appearance. If this were not done, the range position of the test specimen image could be distorted in the lower left and right corners of the sector image. The wiggle phase compensation circuit 1066 is provided in order that left-going and right-going transducer sweeps produce images that do not wiggle sideways. The multi-position switches shown at 1068, 1024 and 1046 cause the master timer module 280, the line waveform and the theta waveform to have the proper proportions for the 10, 15 and 20 centimeter magnification, for example, in the displayed raster size.

Figure 49:
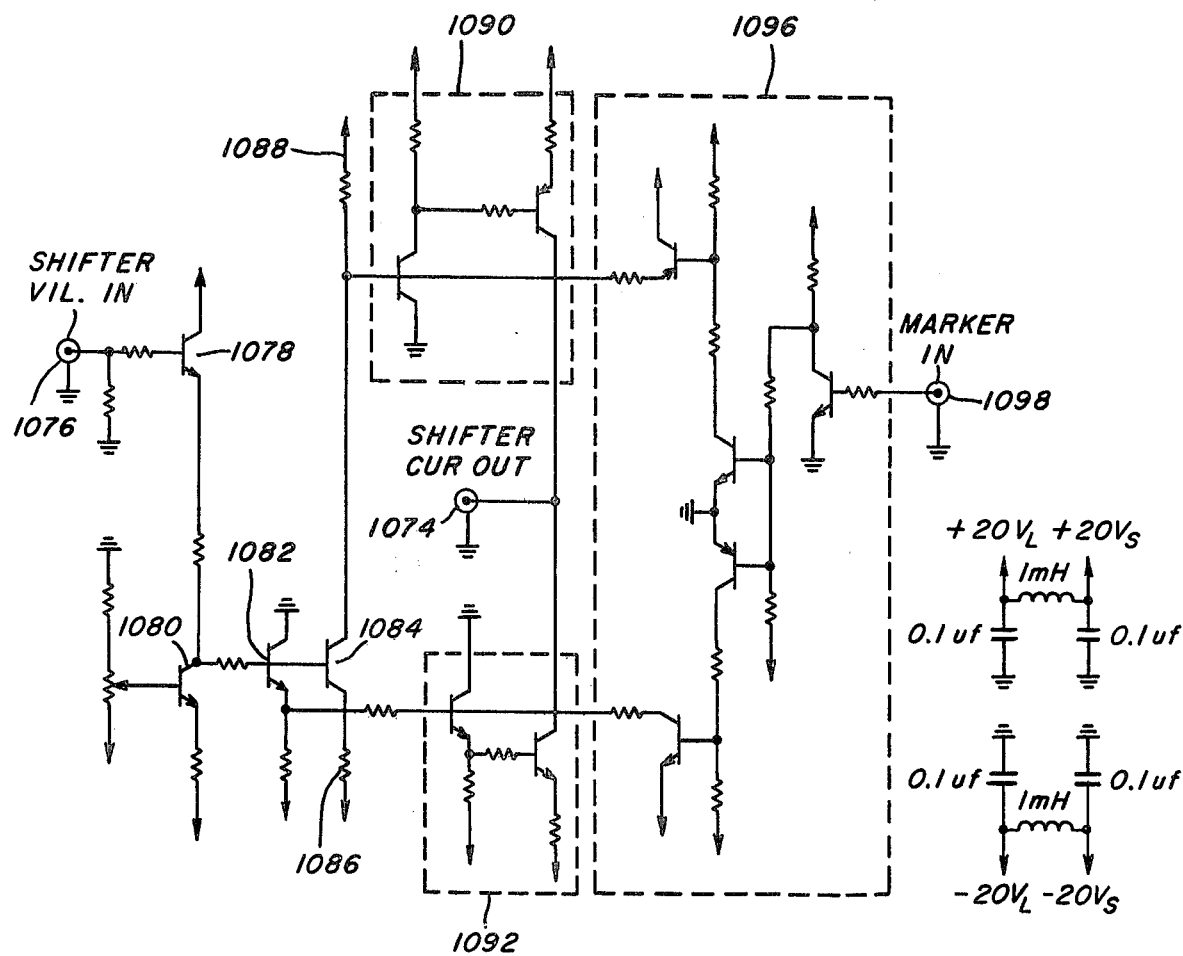
FIG. 49 discloses a form of circuit for the azimuth power unit suitable for use in the present invention.

Referring now to FIGS. 16 and 49, consideration will be given to a form of circuit which is suitable for use as the azimuth power unit 364. The azimuth power unit 364 produces a shifting current into the secondary deflection yoke of the cathode-ray tube assembly 374 that is indirectly connected to the output 1074. The tap video signal from the contrastor module 360 is fed into the azimuth power unit at input 1076 (FIG. 49) by way of lead 366 (FIG. 16). Transistors 1078, 1080, 1082 operate transistor 1084 in order that a replica of the video signal exists to cross each of resistors 1086, 1088. The objective is to make available a video drive voltage at 1088 that is referenced to $+V_{cc}$ (+20v) and to make available a video driving voltage at 1086 that is referenced to $-V_{cc}(-20v)$. These two drive voltages are of opposite polarities, and each voltage activates current sources 1090, 1092, respectively. Current sources 1090, 1092 are capable of delivering considerable current, ranging from about 0 to 1 ampere, for example, depending upon the amplitude of the video signal received at input 1076. Only one current source 1090, 1092 is active at a given time.

Figure 50A:
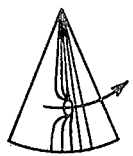
FIGS. 50(a) and 50(b) illustrate a form of azimuth sector display.
Figure 50B:
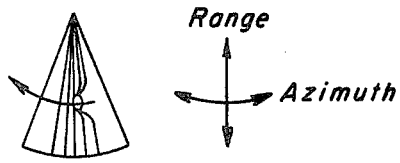

When the displayed sector scan moves from left to right on the cathode-ray tube screen 394, the upper current source 1090 is active, and increasing intensities of video signals cause the sector scanning lines to "bunch together" toward the right. However, when the sector scan moves to the left, the lower current source 1092 is activated in scanning lines bunched to the left. Because of this azimuthal bunching action, the effect of resolution is enhanced in the azimuthal direction. These concepts are illustrated in FIGS. 50(a) and 50(b), wherein the direction of scan is indicated by the arrow superimposed upon the scan lines. Circuitry 1096 (FIG. 49) effects the transition and allows either current source 1090 or current source 1092 to be active, but not both. The command signal for the transition is received at input 1098 from the marker output from sectoring programmer 286 over lead 1100.

Figure 51:
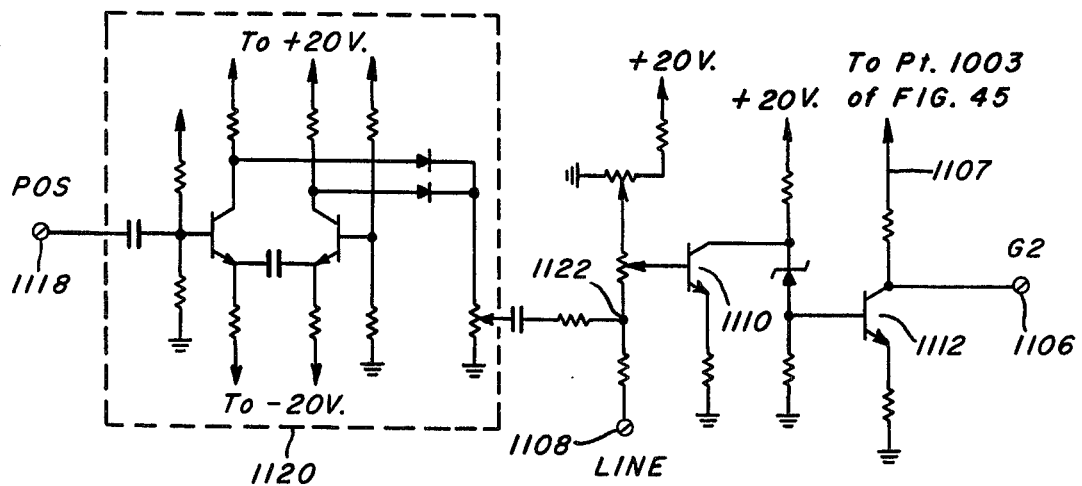
FIG. 51 illustrates a form of circuit for a dynamic intensity compensator suitable for use in the present invention.
Figure 52:
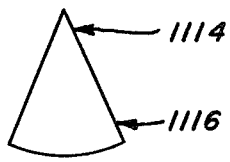
FIG. 52 illustrates schematically a form of sector presentation of the present invention.

Referring now to FIGS. 16 and 51, a suitable form of circuit for dynamic intensity compensator 450 will now be considered. The dynamic intensity compensator 450 serves to adjust the accelerating voltage applied to G2 input 454 of cathode-ray tube assembly 374 via lead 456. This serves to make the intensity of the displayed cathode-ray tube image gradually increase as the sector fans out from top to bottom. This intensity modulation results in a uniform cathode-ray tube brightness of presentation. In the representation of the fan-shaped image shown in FIG. 52, the sector indicated generally by the number 1114 will be of relatively low intensity as contrasted with the sector indicated by the reference number 1116. The line deflection signal from sector display sweep generator 398 (FIG. 16) is applied through lead 412, 458 at point 1108 and is amplified by transistors 1110, 1112 in order that about +2 to +6 volts ramp waveform is increased to about +300 to +350 volts, for example.

As the mechanical motion of transducer 306 is not a perfectly "sharp" triangular wave, but rather has rounded corners, means are preferably provided to reduce the intensity on the left and right-hand edges of the sector fan raster. The position signal at 1118 from the diamond gate sample and hold module 284 (provided through leads 1058, 459) is differentiated and rectified at amplifier 1120. The edges of the sector scan are represented as negative voltage pulses that depress the intensity by combination with the line signal at point 1122.

Figure 53:
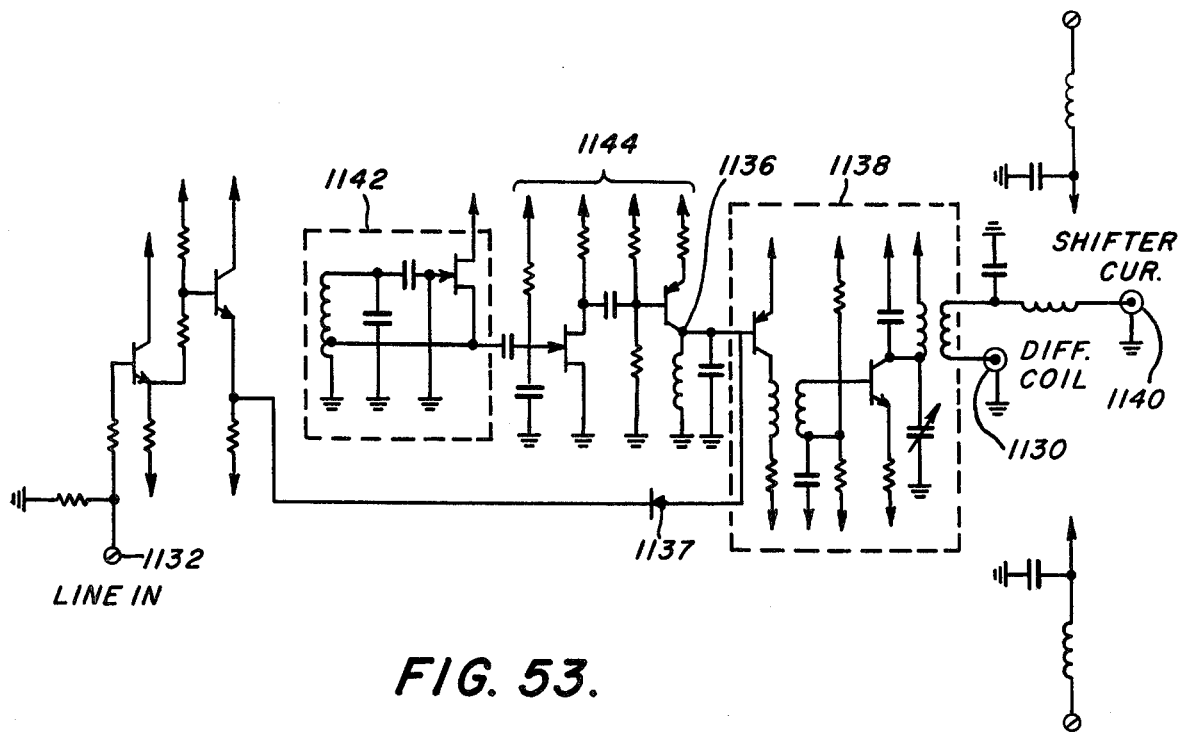
FIG. 53 illustrates a form of a circuit for line width module suitable for use in the present invention.

Referring now to FIGS. 16 and 53, a suitable form of circuit for the line width module 368 will be considered. The line width module 368 provides a radio frequency dithering current available at point 1130 that is applied to the secondary deflection yoke of the cathode-ray tube assembly 374 through lead 376. This serves to produce the controlled, horizontal, astigmatic effect in proportion to the downward deflection along the sector raster. The dither rate is so fast (on the order of 5.0 MHz, for example), that the scan line appears as a smooth band of increasing width. The line deflection signal is applied at input 1132 (FIG. 53) via lead 461 (FIG. 16) and serves to modulate the radio frequency voltage at point 1136. The wedging dither action is illustrated schematically at FIG. 54. The input signal at point 1132 is shown schematically in FIG. 55 and the signal at point 1136 is shown schematically in FIG. 56. It is noted that the timing of increasing dithering action corresponds to the downward, expanding portions of the sector scan raster. Amplifier 1138 raises the signal level at 1136 to approximately 40 volts peak-to-peak at 1130 resulting in about 0.6 amperes peak-to-peak deflection current in the secondary deflection yoke of cathode-ray tube assembly 374. The shifter current from the azimuth power unit 364 is applied through point 1140. Oscillator 1142 provides the 5.0 MHz dither frequency and amplifier 1144 provides the radio frequency constant current source that feeds the modulator section 1136, by changing the reference voltage on clamping diode 1137.

Figure 58:
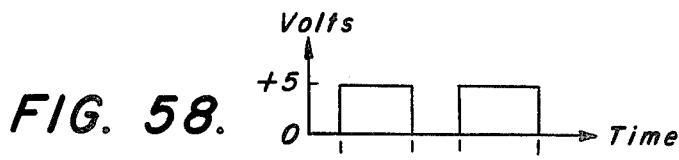
FIGS. 58 through 60 show voltage versus time plots of signals being processed by the equipment of the present invention.
Figure 59:
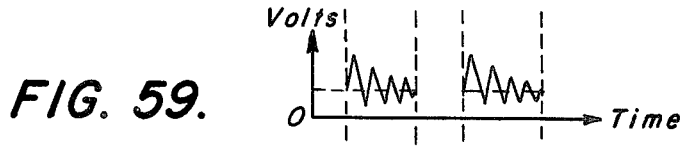
Figure 60:
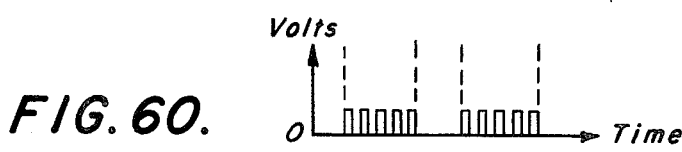
Figure 61:
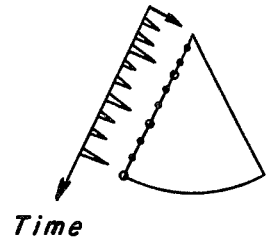
FIG. 61 illustrates a fragmentary, schematic representation of a portion of sector display.

Referring now to FIGS. 16 and 57, a suitable form of circuit for use in connection with marker module 386 (FIG. 16) is shown. The active gate pulse is applied to the marker module through leads 312, 406 at input 1152. This serves to activate oscillations of the phase synchronous tone-burst generator 1154. The pulse forming circuit 1156 converts the damp, sinusoidal oscillation at point 1158 into short square pulses at point 1160. FIG. 58 illustrates a form of active gate pulse such as that received in input 1152. The generator output at point 1158 is shown in FIG. 59, and the pulse output at 1160 is shown in FIG. 60. The pulses at point 1160 are available at point 1166 and are fed into one-half of the mixer amplifier 1168. The output of this amplifier at 1170 is normally clamped by circuit 1172 plus the marker pulse from the sectoring programmer 286 (FIG. 16) received at 1174 over lead 1176 (FIG. 16) causes circuit 1172 to release the clamping action. Such a release normally occurs at the left edge of the sector raster. Meanwhile, the digital integrated divide by 6, 12 counter circuit 1178 divides the count by three so that one pulse is available on lead 1180 for every three trigger pulses at point 1160. (The integrated circuit 1178 may conveniently be a standard TTL Type SN7492.) Circuit 1182 retards the first divide by three count of circuit 1178 in order that the first three 1.0 cm. marks occur in the correct location. The output of the integrated circuit at point 1184 drives the right half of the mixer amplifier at 1168. The output at 1186 represents a combination of dim and bright dots, such as is shown schematically in FIG. 61, and the total marker intensities are governed by the settings of potentiometer 1187.

Figure 62:
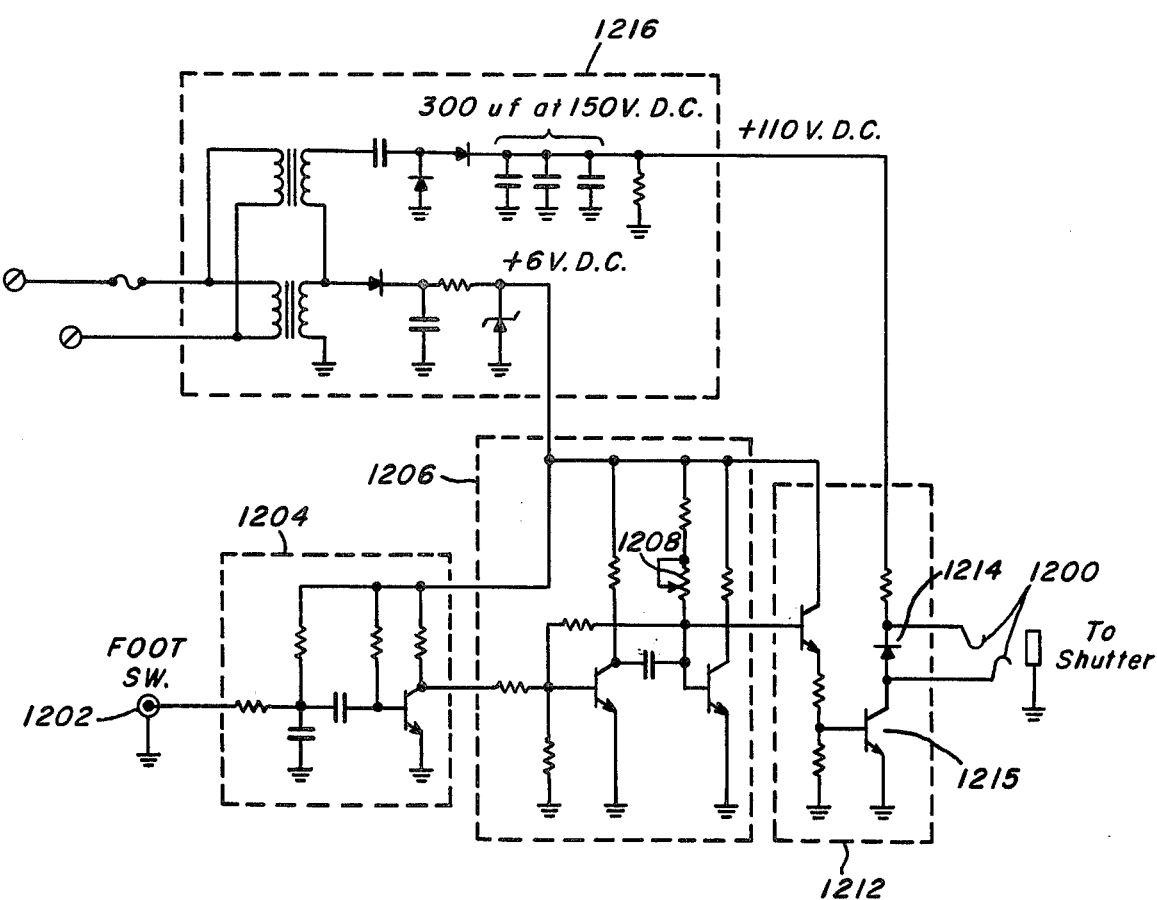
FIG. 62 illustrates a form of circuit suitable for use in the camera control of the present invention.

Referring now to FIGS. 16 and 62, a form of circuitry adapted for use in connection with the camera system of the present apparatus will now be considered. The camera control 428 (FIG. 16) provides a control duration current pulse to the shutter connection of camera 426 at points 1200 (FIG. 62). When switch 430 closes, contact 1202 is closed and circuit 1204 triggers the one-shot multivibrator 1206 to produce a pulse ranging from about 0.1 to 0.7 seconds, for example, depending upon the setting of potentiometer 1208. Power amplifier 1212 supplies a 100 volt shutter pulse to points 1200. Diode 1214 protects transistor 1215 from burnout due to inductive kick-back emf (electromotive force) of the shutter solenoid. Circuit 1216 supplies the low voltage (+6.0 volts DC) and the high voltage (+110 volts DC) needed to operate the signal (timing) and power handling (shutter) circuits, respectively.

While dimensions form no part of the present invention per se, it is contemplated that the sealed housing within which the transducer is mounted may consist of a cylindrical housing having a diameter of about 1.25 to 1.75 inches and a height of about 1.75 to 3.25 inches, with a weight of about 2 to 8 ounces.

It will therefore be appreciated that the present invention has provided ultrasonic scanning apparatus wherein an ultrasonic transducer is moved through a predetermined path by magnetic means. Means are provided for determining the actual position of the transducer within the predetermined path, and, if desired, effecting a change in order to correct for any departure from the desired position within the predetermined path. Means are provided for processing the data received from the moving transducer in order to provide a real-time visual display or any other desired form of information readout, such as a storage cathode-ray tube, or a printout, such as an electrostatic hard copy, for example. All of this is accomplished without the need to place primary reliance upon either manual movement of the transducer through an angular orbit or to use rigid mechanical linkage or electronic transducer array substitutes therefor. As a result, efficient movement coupled with servo concept insurance of accuracy of positioning is effected in an economical fashion. Also, as a result of the low inertia of the mechanical elements, such as the transducer-permanent magnet assembly of FIGS. 1-4, for example, the system remains highly responsive to motion command signals.

While for convenience of reference and clarity of illustration herein, various words of orientation, such as "front," "rear," "top," "bottom," "left," "right" and similar words have been employed, it will be appreciated that unless expressly indicated to the contrary in a particular use, these are purely illustrative and not limiting upon the scope of the invention.

The electronic signal processing means (or portions thereof) of the present invention may conveniently be located within a sealed portion of the interior of the housing in a fashion so as not to have damaging contact with the fluid within the housing or, in the alternative, may be placed exteriorly of the housing. Also, a system is expressly contemplated wherein the entire unit is composed of integrated circuits contained within a small flashlight-like housing, adapted to be readily held in the hand with a transducer mounted for angular movement disposed at one end and a cathode-ray tube at the other end.

It will further be appreciated that the present system provides an economical means of providing a portable, ultrasonic scanner having precisely controlled transducer movement and adapted for use in a wide variety of environments in addition to hospitals, such as clinics and physicians' offices. The system may be adapted for a wide range of both medical and non-medical uses without departing from the basic teachings of the invention. If desired, for example, automatic means may be provided for moving the scanner along a linear path while the transducer is moved in a predetermined angular path as disclosed herein. For example, sterilizable heads may be employed in a wide variety of medical uses where such equipment is desirable as, for example, opthamology, carrotid artery plaque examination, fetal cardiac and respiration examinations and echocardiography.

While for purposes of clarity of illustration, reference has been made herein to "B-scan" ultrasonic procedures, it will be appreciated that the apparatus of the invention may readily be adapted for use in other procedures (including "A-scan" and through scan procedures) without departing from the principles of the invention.

Whereas, particular embodiments of the invention have been described above for purposes of illustration, it will be evident to those skilled in the art, that numerous variations of the details may be made without departing from the invention as defined in the appended claims.

I claim:

1. Ultrasonic scanning apparatus for insonifying a specimen comprising:
   a housing,
   an ultrasonic transducer disposed within said housing and mounted for movement in a predetermined path therewithin,
   magnetic means for effecting movement of said transducer in said predetermined path,
   electrical means for energizing said transducer and receiving signals therefrom,
   said magnetic means including permanent magnet means and electromagnetic means,
   energizing means for electrically energizing said electromagnetic means,
   position sensing means for determining the position of said transducer within said predetermined path,
   said position sensing means being disposed out of direct physical contact with said specimen, and
   signal processing means for comparing a position signal from said position sensing means and another signal which indicates a desired position of said transducer and emitting a position correcting signal if a difference in said signals exists, whereby
   said transducer may be moved in a continuously controlled manner in said predetermined path within said housing independently of the position or movement of said housing with automatic correction for departures of said transducer from a desired position on said predetermined path, by position sensing means disposed out of direct physical contact with said specimen and cooperating with said signal processing means.

2. The ultrasonic scanning apparatus of claim 1 including said transducer being a focussed transducer.

3. The ultrasonic scanning apparatus of claim 2 including;
   said transducer being secured to said permanent magnet means, and
   bearing means supporting said permanent magnet-transducer assembly for rotational movement.

4. Ultrasonic scanning apparatus comprising
   a housing,
   an ultrasonic transducer disposed within said housing and mounted for movement in a predetermined path therewithin,
   magnetic means for effecting movement of said transducer in said predetermined path,
   electrical means for energizing said transducer and receiving signals therefrom,
   said magnetic means including permanent magnet means and electromagnetic means,
   energizing means for electrically energizing said electromagnetic means,
   position sensing means for determining the position of said transducer within said predetermined path,
   said transducer being a focussed transducer,
   said transducer being secured to said permanent magnet means, bearing means supporting said permanent magnet-transducer assembly for rotational movement, support means having depending legs disposed on opposed sides of said permanent magnet-transducer assembly, and said bearing means being in contact with and supported by said depending legs.

5. The ultrasonic scanning apparatus of claim 3 including said permanent magnet means being so secured to said transducer as to provide damping for said transducer's acoustical behavior.

6. The ultrasonic scanning apparatus of claim 4 including said electrical means including a first pair of electrically conductive lead means for connecting said transducer with said bearing means and a second pair of electrically conductive lead means for connecting said support means with the exterior of said housing, whereby said bearing means serves to commutate signals into and out of said transducer.

7. The ultrasonic scanning apparatus of claim 4 including said bearing means being needle bearings.

8. The ultrasonic scanning apparatus of claim 7 including said needle bearings being secured to generally opposed sides of said permanent magnet means.

9. The ultrasonic scanning apparatus of claim 7 including said electromagnetic means including magnetic elements having portions disposed adjacent to said permanent magnet means, coil means wrapped around said magnetic elements, and said coil means electrically energized by said energizing means.

10. The ultrasonic scanning apparatus of claim 9 including said coil means being a unitary coil wrapped around both said magnetic elements.

11. The ultrasonic scanning apparatus of claim 9 including said coil means being a pair of coils, each being wrapped around one said magnetic element.

12. The ultrasonic scanning apparatus of claim 1 including said position sensing means including a light source, photosensitive means and vane means so positioned that movement of said transducer in said predetermined path will alter the amount of light received from said light source by said photosensitive means.

13. The ultrasonic scanning apparatus of claim 12 including said photosensitive means including phototransistor means.

14. The ultrasonic scanning apparatus of claim 3 including said position sensing means including vane means secured to said permanent magnet-transducer assembly, a light source and photosensitive means, whereby rotation of said permanent magnet-transducer assembly about said bearing means will alter the amount of light received from said light source by said photosensitive means.

15. The ultrasonic scanning apparatus of claim 14 including said photosensitive means including phototransistor means.

16. The ultrasonic scanning apparatus of claim 1 including said position sensing means including eddy current vanes and variable inductance coils, and said eddy current vanes being operatively associated with said variable inductance coils, whereby the eddy currents induced within such vanes will vary with changes in said transducer position.

17. The ultrasonic scanning apparatus of claim 3 including said position sensing means including eddy current vanes secured to said permanent magnet-transducer assembly and variable inductance coils, and said eddy current vanes being operatively associated with said variable inductance coils, whereby rotation of said permanent magnet-transducer assembly about said bearing means will alter the eddy current induced within said vanes.

18. Ultrasonic scanning apparatus comprising a housing, an ultrasonic transducer disposed within said housing and mounted for movement in a predetermined path therewithin, magnetic means for effecting movement of said transducer in said predetermined path, electrical means for energizing said transducer and receiving signals therefrom, said magnetic means including permanent magnet means and electromagnetic means, energizing means for electrically energizing said electromagnetic means, position sensing means for determining the position of said transducer within said predetermined path, said transducer being a focussed transducer, said transducer being secured to said permanent magnet means, bearing means supporting said permanent magnet-transducer assembly for rotational movement, said scanning apparatus being an invasive medical procedure apparatus, said permanent magnet means having an opening therethrough, said transducer having an opening therethrough generally aligned with said permanent magnet openings, and said housing having an opening defining portion which passes through said permanent magnet opening and said transducer opening, whereby a syringe or other medical instrument may be passed through said openings.

19. The ultrasonic scanning apparatus of claim 18 including said openings being generally coaxial with the central longitudinal axis of said housing.

20. The ultrasonic scanning apparatus of claim 18 including said openings being generally radially oriented slots and, said slots being disposed in circumferential discontinuities in said permanent magnet means, said transducer and said housing.

21. The ultrasonic scanning apparatus of claim 18 including and permanent magnet means being of a generally annular shape, said transducer being of generally annular shape, and the opening defining portion of said housing having an external surface which is spaced inwardly from the surfaces defining said openings in said permanent magnet means and said transducer, whereby said transducer may be rotated in said predetermined path without undesired mechanical interference from said opening defining portion.

within which the transducer is mounted may consist of a cylindrical housing having a diameter of about 1.25 to 1.75 inches and a height of about 1.75 to 3.25 inches, with a weight of about 2 to 8 ounces.

It will therefore be appreciated that the present invention has provided ultrasonic scanning apparatus wherein an ultrasonic transducer is moved through a predetermined path by magnetic means. Means are provided for determining the actual position of the transducer within the predetermined path, and, if desired, effecting a change in order to correct for any departure from the desired position within the predetermined path. Means are provided for processing the data received from the moving transducer in order to provide a real-time visual display or any other desired form of information readout, such as a storage cathode-ray tube, or a printout, such as an electrostatic hard copy, for example. All of this is accomplished without the need to place primary reliance upon either manual movement of the transducer through an angular orbit or to use rigid mechanical linkage or electronic transducer array substitutes therefor. As a result, efficient movement coupled with servo concept insurance of accuracy of positioning is effected in an economical fashion. Also, as a result of the low inertia of the mechanical elements, such as the transducer-permanent magnet assembly of FIGS. 1-4, for example, the system remains highly responsive to motion command signals.

While for convenience of reference and clarity of illustration herein, various words of orientation, such as "front," "rear," "top," "bottom," "left," "right" and similar words have been employed, it will be appreciated that unless expressly indicated to the contrary in a particular use, these are purely illustrative and not limiting upon the scope of the invention.

The electronic signal processing means (or portions thereof) of the present invention may conveniently be located within a sealed portion of the interior of the housing in a fashion so as not to have damaging contact with the fluid within the housing or, in the alternative, may be placed exteriorly of the housing. Also, a system is expressly contemplated wherein the entire unit is composed of integrated circuits contained within a small flashlight-like housing, adapted to be readily held in the hand with a transducer mounted for angular movement disposed at one end and a cathode-ray tube at the other end.

It will further be appreciated that the present system provides an economical means of providing a portable, ultrasonic scanner having precisely controlled transducer movement and adapted for use in a wide variety of environments in addition to hospitals, such as clinics and physicians' offices. The system may be adapted for a wide range of both medical and non-medical uses without departing from the basic teachings of the invention. If desired, for example, automatic means may be provided for moving the scanner along a linear path while the transducer is moved in a predetermined angular path as disclosed herein. For example, sterilizable heads may be employed in a wide variety of medical uses where such equipment is desirable as, for example, opthamology, carrotid artery plaque examination, fetal cardiac and respiration examinations and echocardiography.

While for purposes of clarity of illustration, reference has been made herein to "B-scan" ultrasonic procedures, it will be appreciated that the apparatus of the invention may readily be adapted for use in other procedures (including "A-scan" and through scan procedures) without departing from the principles of the invention.

Whereas, particular embodiments of the invention have been described above for purposes of illustration, it will be evident to those skilled in the art, that numerous variations of the details may be made without departing from the invention as defined in the appended claims.

I claim:

1. Ultrasonic scanning apparatus for insonifying a specimen comprising:
   a housing,
   an ultrasonic transducer disposed within said housing and mounted for movement in a predetermined path therewithin,
   magnetic means for effecting movement of said transducer in said predetermined path,
   electrical means for energizing said transducer and receiving signals therefrom,
   said magnetic means including permanent magnet means and electromagnetic means,
   energizing means for electrically energizing said electromagnetic means,
   position sensing means for determining the position of said transducer within said predetermined path,
   said position sensing means being disposed out of direct physical contact with said specimen, and
   signal processing means for comparing a position signal from said position sensing means and another signal which indicates a desired position of said transducer and emitting a position correcting signal if a difference in said signals exists, whereby
   said transducer may be moved in a continuously controlled manner in said predetermined path within said housing independently of the position or movement of said housing with automatic correction for departures of said transducer from a desired position on said predetermined path, by position sensing means disposed out of direct physical contact with said specimen and cooperating with said signal processing means.

2. The ultrasonic scanning apparatus of claim 1 including said transducer being a focussed transducer.

3. The ultrasonic scanning apparatus of claim 2 including;
   said transducer being secured to said permanent magnet means, and
   bearing means supporting said permanent magnet-transducer assembly for rotational movement.

4. Ultrasonic scanning apparatus comprising
   a housing,
   an ultrasonic transducer disposed within said housing and mounted for movement in a predetermined path therewithin,
   magnetic means for effecting movement of said transducer in said predetermined path,
   electrical means for energizing said transducer and receiving signals therefrom,
   said magnetic means including permanent magnet means and electromagnetic means,
   energizing means for electrically energizing said electromagnetic means,
   position sensing means for determining the position of said transducer within said predetermined path,
   said transducer being a focussed transducer,
   said transducer being secured to said permanent magnet means, bearing means supporting said permanent magnet-transducer assembly for rotational movement, support means having depending legs disposed on opposed sides of said permanent magnet-transducer assembly, and said bearing means being in contact with and supported by said depending legs.

5. The ultrasonic scanning apparatus of claim 3 including said permanent magnet means being so secured to said transducer as to provide damping for said transducer's acoustical behavior.

6. The ultrasonic scanning apparatus of claim 4 including said electrical means including a first pair of electrically conductive lead means for connecting said transducer with said bearing means and a second pair of electrically conductive lead means for connecting said support means with the exterior of said housing, whereby said bearing means serves to commutate signals into and out of said transducer.

7. The ultrasonic scanning apparatus of claim 4 including said bearing means being needle bearings.

8. The ultrasonic scanning apparatus of claim 7 including said needle bearings being secured to generally opposed sides of said permanent magnet means.

9. The ultrasonic scanning apparatus of claim 7 including said electromagnetic means including magnetic elements having portions disposed adjacent to said permanent magnet means, coil means wrapped around said magnetic elements, and said coil means electrically energized by said energizing means.

10. The ultrasonic scanning apparatus of claim 9 including said coil means being a unitary coil wrapped around both said magnetic elements.

11. The ultrasonic scanning apparatus of claim 9 including said coil means being a pair of coils, each being wrapped around one said magnetic element.

12. The ultrasonic scanning apparatus of claim 1 including said position sensing means including a light source, photosensitive means and vane means so positioned that movement of said transducer in said predetermined path will alter the amount of light received from said light source by said photosensitive means.

13. The ultrasonic scanning apparatus of claim 12 including said photosensitive means including phototransistor means.

14. The ultrasonic scanning apparatus of claim 3 including said position sensing means including vane means secured to said permanent magnet-transducer assembly, a light source and photosensitive means, whereby rotation of said permanent magnet-transducer assembly about said bearing means will alter the amount of light received from said light source by said photosensitive means.

15. The ultrasonic scanning apparatus of claim 14 including said photosensitive means including phototransistor means.

16. The ultrasonic scanning apparatus of claim 1 including said position sensing means including eddy current vanes and variable inductance coils, and said eddy current vanes being operatively associated with said variable inductance coils, whereby the eddy currents induced within such vanes will vary with changes in said transducer position.

17. The ultrasonic scanning apparatus of claim 3 including said position sensing means including eddy current vanes secured to said permanent magnet-transducer assembly and variable inductance coils, and said eddy current vanes being operatively associated with said variable inductance coils, whereby rotation of said permanent magnet-transducer assembly about said bearing means will alter the eddy current induced within said vanes.

18. Ultrasonic scanning apparatus comprising a housing, an ultrasonic transducer disposed within said housing and mounted for movement in a predetermined path therewithin, magnetic means for effecting movement of said transducer in said predetermined path, electrical means for energizing said transducer and receiving signals therefrom, said magnetic means including permanent magnet means and electromagnetic means, energizing means for electrically energizing said electromagnetic means, position sensing means for determining the position of said transducer within said predetermined path, said transducer being a focussed transducer, said transducer being secured to said permanent magnet means, bearing means supporting said permanent magnet-transducer assembly for rotational movement, said scanning apparatus being an invasive medical procedure apparatus, said permanent magnet means having an opening therethrough, said transducer having an opening therethrough generally aligned with said permanent magnet openings, and said housing having an opening defining portion which passes through said permanent magnet opening and said transducer opening, whereby a syringe or other medical instrument may be passed through said openings.

19. The ultrasonic scanning apparatus of claim 18 including said openings being generally coaxial with the central longitudinal axis of said housing.

20. The ultrasonic scanning apparatus of claim 18 including said openings being generally radially oriented slots and, said slots being disposed in circumferential discontinuities in said permanent magnet means, said transducer and said housing.

21. The ultrasonic scanning apparatus of claim 18 including and permanent magnet means being of a generally annular shape, said transducer being of generally annular shape, and the opening defining portion of said housing having an external surface which is spaced inwardly from the surfaces defining said openings in said permanent magnet means and said transducer, whereby said transducer may be rotated in said predetermined path without undesired mechanical interference from said opening defining portion.

UNITED STATES PATENT AND TRADEMARK OFFICE
CERTIFICATE OF CORRECTION

PATENT NO. : 4,092,867
DATED : June 6, 1978
INVENTOR(S) : Terrance Matzuk

It is certified that error appears in the above-identified patent and that said Letters Patent are hereby corrected as shown below:

Cover Sheet. Under "References cited" add:

OTHER REFERENCES -- W. H. Schuette et al, "Real-Time Two Dimensional Mechanical Ultrasonic Sector Scanner with Electronic Control of Sector Width, Abstract of Article July 7, 1976, 73-67.8S"

Column 15, line 47 change "383" to -- 382 --.

Signed and Sealed this

Fourth Day of *December 1979*

[SEAL]

*Attest:*

SIDNEY A. DIAMOND

*Attesting Officer*   *Commissioner of Patents and Trademarks*